(12) United States Patent
Rheineck et al.

(10) Patent No.: US 11,839,447 B2
(45) Date of Patent: Dec. 12, 2023

(54) WEARABLE OPEN AND ADJUSTABLE MRI HEAD COIL

(71) Applicant: MR Instruments, Inc., Minneapolis, MN (US)

(72) Inventors: Thomas J Rheineck, Chanhassen, MN (US); Mark Jensen, Hopkins, MN (US); Michael Lancial, Saint Louis Park (MN); Grant Thompson, Saint Paul, MN (US); Leon Ricord, Waconia, MN (US); Juan Martinez, Houlton, MN (US); Robert Bushey, Coon Rapids, MN (US); Brian Fabian, Shakopee, MN (US); Khai Tran, Chanhassen, MN (US); Lawrence Tanenbaum, Riverside, CT (US)

(73) Assignee: MR Instruments, Inc., Minneapolis, MN (US)

( * ) Notice: Subject to any disclaimer, the term of this patent is extended or adjusted under 35 U.S.C. 154(b) by 0 days.

(21) Appl. No.: 16/617,350

(22) PCT Filed: Jan. 15, 2019

(86) PCT No.: PCT/US2019/013639
§ 371 (c)(1),
(2) Date: Nov. 26, 2019

(87) PCT Pub. No.: WO2019/209389
PCT Pub. Date: Oct. 31, 2019

(65) Prior Publication Data
US 2021/0121066 A1 Apr. 29, 2021

Related U.S. Application Data

(60) Provisional application No. 62/661,392, filed on Apr. 23, 2018.

(51) Int. Cl.
*A61B 5/00* (2006.01)
*A61B 5/055* (2006.01)
(Continued)

(52) U.S. Cl.
CPC .......... *A61B 5/0035* (2013.01); *A61B 5/0015* (2013.01); *A61B 5/055* (2013.01);
(Continued)

(58) Field of Classification Search
CPC ..... A61B 5/0035; A61B 5/0015; A61B 5/055; A61B 8/4227; A61B 5/6803; G01R 33/34007; G01R 33/34084; G01R 33/4814
See application file for complete search history.

(56) References Cited

U.S. PATENT DOCUMENTS 6,155,974 A * 12/2000 Fish ..................... A61B 5/0006
128/903
6,163,240 A 12/2000 Zuk et al.
(Continued)

FOREIGN PATENT DOCUMENTS

CA   3097828 A1   10/2019
CN   107773241 A * 3/2018 ............. A61B 5/055
(Continued)

OTHER PUBLICATIONS

"European Application Serial No. 19792180.2, Extended European Search Report dated Jul. 2, 2021", 11 pgs.
(Continued)

*Primary Examiner* — Colin T. Sakamoto
*Assistant Examiner* — Tommy T Ly
(74) *Attorney, Agent, or Firm* — Schwegman Lundberg & Woessner, P.A.

(57) ABSTRACT

A wearable, open and adjustable MRI head coil system having an assembly of support members, panels, or portions
(Continued)

defining one or more access openings. The support members, panels, or portions can support, house, or otherwise include radiofrequency receiver antennae or imaging coils such that the assembly is positionable or wearable by a patient for MRI scanning. The radiofrequency receiver antennae or imaging coils, and other devices can be simultaneously in contact with a patient's head, thereby enabling use during diagnostic, therapeutic, surgical, or other interventional procedures.

22 Claims, 19 Drawing Sheets

(51) Int. Cl.
    *A61B 8/00*     (2006.01)
    *G01R 33/34*     (2006.01)
    *G01R 33/48*     (2006.01)

(52) U.S. Cl.
    CPC ...... *A61B 8/4227* (2013.01); *G01R 33/34007* (2013.01); *G01R 33/34084* (2013.01); *G01R 33/4814* (2013.01)

(56) References Cited

U.S. PATENT DOCUMENTS

| | | | |
|---|---|---|---|
| 7,345,483 B2 | 3/2008 | Vaughan | |
| 7,619,413 B2 | 11/2009 | Wiggins | |
| 7,887,488 B2 | 2/2011 | Masters | |
| 8,406,853 B2 | 3/2013 | Petropoulos | |
| 8,487,615 B2 | 7/2013 | Zhu et al. | |
| 8,570,037 B2 | 10/2013 | Schellekens et al. | |
| 8,604,789 B2 | 12/2013 | Shvartsberg et al. | |
| 8,797,029 B2 | 8/2014 | Zhu et al. | |
| 8,952,694 B2* | 2/2015 | Biber | G01R 33/34061 324/318 |
| 9,204,818 B2 | 12/2015 | Moffatt | |
| 9,554,779 B2 | 1/2017 | Larson et al. | |
| 9,958,517 B2 | 5/2018 | Biber et al. | |
| 10,765,403 B2 | 9/2020 | Tretbar et al. | |
| 10,827,948 B1* | 11/2020 | Tramm | A61B 5/7405 |
| 10,895,615 B2 | 1/2021 | Wynn et al. | |
| 2008/0007259 A1* | 1/2008 | Driemel | G01R 33/3415 600/410 |
| 2008/0306377 A1 | 12/2008 | Piron et al. | |
| 2009/0227852 A1* | 9/2009 | Glaser | A61B 5/6816 341/20 |
| 2010/0296723 A1 | 11/2010 | Greer et al. | |
| 2010/0312093 A1 | 12/2010 | Biglieri et al. | |
| 2012/0062233 A1 | 3/2012 | Reykowski | |
| 2012/0112748 A1 | 5/2012 | Hetherington et al. | |
| 2012/0265052 A1 | 10/2012 | Rohr et al. | |
| 2012/0265053 A1 | 10/2012 | Rohr et al. | |
| 2013/0317346 A1* | 11/2013 | Alagappan | G01R 33/34046 600/415 |
| 2014/0213886 A1 | 7/2014 | Menon et al. | |
| 2015/0112187 A1 | 4/2015 | Petropoulos et al. | |
| 2015/0265365 A1 | 9/2015 | Andrews et al. | |
| 2015/0265366 A1* | 9/2015 | Andrews | A61B 18/1477 600/417 |
| 2015/0265857 A1 | 9/2015 | Barnes et al. | |
| 2016/0062233 A1 | 3/2016 | Masuyama et al. | |
| 2016/0256713 A1 | 9/2016 | Saunders et al. | |
| 2016/0291100 A1 | 10/2016 | Ha et al. | |
| 2016/0354175 A1 | 12/2016 | Andrews et al. | |
| 2017/0209070 A1 | 7/2017 | Rohr et al. | |
| 2017/0248666 A1* | 8/2017 | Rothgang | G01R 33/3415 |
| 2017/0296289 A1 | 10/2017 | Andrews et al. | |
| 2018/0070852 A1 | 3/2018 | Azulay et al. | |
| 2018/0310894 A1* | 11/2018 | Gallant | A61B 6/04 |
| 2019/0154774 A1* | 5/2019 | Hushek | G01R 33/3415 |
| 2022/0409085 A1 | 12/2022 | Instruments | |

FOREIGN PATENT DOCUMENTS

| | | | | |
|---|---|---|---|---|
| EP | | 3721245 A1 | 10/2020 | |
| WO | WO-2017143444 A1 * | | 8/2017 | ............. A61B 5/055 |
| WO | WO2017143444 A1 | | 8/2017 | |
| WO | WO-2019209389 A1 | | 10/2019 | |
| WO | WO-2021108773 A1 | | 6/2021 | |

OTHER PUBLICATIONS

"European Application Serial No. 19792180.2, Response filed Jan. 27, 2022 to Extended European Search Report dated Jul. 2, 2021", 12 pgs.

Harvey, Paul R., et al., "MultiTransmit parallel RFtransmission technology", (Aug. 10, 2010), 16 pgs.

Zhou, Anqi, "RF Coils in MRI", (May 19, 2006), 33 pgs.

Fabian Kording et al., Evaluation of a Portable Doppler Ultrasound Gating Device for Fetal Cardiac MR Imaging: Initial Results at 1.5T and 3T, Magn Reson Med Sci 2018; 17; 308-317, Japanese Society for Magnetic Resonance in Medicine.

"U.S. Appl. No. 17/756,280 Preliminary Amendment Filed with Application", (7 pgs.).

"Chinese Application Serial No. 202090000996.5, Notification to Make Rectification dated Jun. 20, 2022", with machine translation, 3 pgs.

"Chinese Application Serial No. 202090000996.5, Response filed Oct. 20, 2022", with machine translation, 18 pgs.

"International Application Serial No. PCT/US2019/013639, International Preliminary Report on Patentability dated Nov. 5, 2020", 8 pgs.

"International Application Serial No. PCT/US2019/013639, International Search Report dated Apr. 4, 2019", 2 pgs.

"International Application Serial No. PCT/US2019/013639, Written Opinion dated Apr. 4, 2019", 6 pgs.

"International Application Serial No. PCT/US2020/062511, International Preliminary Report on Patentability dated Jun. 9, 2022", 7 pgs.

"International Application Serial No. PCT/US2020/062511, International Search Report dated Feb. 26, 2021", 2 pgs.

"International Application Serial No. PCT/US2020/062511, Written Opinion dated Feb. 26, 2021", 5 pgs.

"Chinese Application Serial No. 202090000996.5, Notification to Make Rectification dated Mar. 14, 2023", w/o English Translation, 3 pgs.

"Chinese Application Serial No. 202090000996.5, Office Action dated Jan. 9, 2023", w/ English Translation, 4 pgs.

"Chinese Application Serial No. 202090000996.5, Response filed Mar. 1, 2023 to Office Action dated Jan. 9, 2023", w/ English claims, 19 pgs.

"European Application Serial No. 20892846.5, Response to Communication pursuant to Rules 161(2) and 162 EPC filed Dec. 28, 2022", 11 pgs.

"Chinese Application Serial No. 202090000996.5, Response filed May 23, 2023 to Notification to Make Rectification dated Mar. 14, 2023", w English claims, 28 pgs.

* cited by examiner

WEARABLE OPEN AND ADJUSTABLE MRI HEAD COIL

PRIORITY

This Application claims priority to PCT Patent Application No. PCT/US2019/013639 filed on Jan. 15, 2019 and which claims the benefit of U.S. Provisional Patent Application No. 62/661,392, filed Apr. 23, 2018, all of which is incorporated fully herein by reference.

FIELD

The present invention is directed to a surface coil imaging system, such as those used in magnetic resonance imaging ("MRI") devices. More particularly, the present invention is directed to a wearable or positionable open surface coil system that is worn or placed on a patient's head and that can be used during diagnostic, therapeutic, and interventional procedures.

BACKGROUND

During the 1970s and 1980s, numerous advancements in medical imaging were made that enabled physicians to better examine and diagnose patients. One such advancement was the magnetic resonance imaging, or MRI device. MRIs permitted physicians to use magnetic fields and radio waves to capture high quality images of internal tissue without having to do exploratory surgery, or exposing patients to high levels of radiation.

Although an MRI can be used to examine the brain, organs, glands, and soft tissues of patients, it has been particularly useful for scanning the head or cranium of patients. An MRI scan is able to render high quality images of the brain and cranial structures. Physicians are able to use an MRI to see abnormalities such as brain bleeding and swelling, aneurysms, stroke, tumors, as well as upper cervical spine injuries and disorders.

Once an abnormality or injury is identified and located, it is possible to use an MRI to support the treatment of patients. For instance, in brain abnormalities, a surgeon may use an MRI while conducting neurosurgery-intervention (e.g., deep brain stimulation ("DBS"), laser ablation, Focus Ultrasound Ablation (or neurosurgery), and the like—known as MR-guided neurotherapy or MR-guided neurosurgery. The ability to use MR-guided neurotherapy significantly increases visibility to the treatment area and improves the outcome of the surgery.

Using an MRI during neurosurgery, however, presents some significant challenges. First, conventional head coils, as illustrated in FIG. 1A, tend to be large rigid structures that fit over a patient's head like an enclosed birdcage, making access virtually impossible. Second, the large rigid head coils make head stabilization, which is critical during neurosurgery, more difficult. During a neurosurgical procedure, a patient's head is held or fixed by a rigid, non-magnetic head frame or holder that is connected to, but spaced apart from, a patient's head. These head holders typically comprise a circular or rectangular frame with pins or screws that are drilled or driven into the patient's head to hold it still. The combination of the head frame with the rigid head coil compounds the difficulty of accessing a particular cranial surgery or therapy site. Additionally, the rigid head coils further add to the claustrophobia experienced by some patients positioned in the enclosed birdcage during routine diagnostic procedures.

In instances where a rigid head coil and head holder cannot be used together, generally flat or semi-flexible surface coils are used to obtain the MRI images. The flat surface coils are designed to be placed as close as possible to the patient's head in order to increase the signal-to-noise ratio. These flat surface coils, while somewhat pliable, are not generally conforming to a patient's head. This lack of pliability, along with the stabilization head frame, results in the distance between the surface coil and the patient's cranium or head to be increased, thereby having a negative impact on the signal-to-noise ratio, and resultingly degrading the image quality.

In MR-guided neurotherapy or neurosurgery, there is a need to have one or more head coils or surface coils that can be comfortably worn by, or placed on, a patient to have a generally consistent, strong, and uniform sign-to-noise ratio. There is also a need to have a comfortable head coil or surface coil that has an open framework that provides physicians and surgeons with greatly improved access to the patient such that therapy and interventional devices like ultrasound transducers, cannula guides, electroencephalography EEG, electromyography EMG, or electronystagmography ENG sensors can be placed flush against a patient's head or body while still providing improved access to a surgical site.

Still another need exists to have a comfortable head or surface coil that has an open framework and/or is adjustable to permit improved access for placement of a head fixation frame or holder. Another need exists to have a comfortable head or surface coil that is adjustable such that it has at least one access panel or openings that can be moved or displaced to provide surgical or therapy site access. Additionally, another need also exists to have a comfortable head coil or surface coil that eliminates or greatly reduces patient claustrophobia for diagnostic exams where the patient is awake.

Yet another need exists to place multiple, pliable surface coils on the head, or on any anatomy, wherein multiple coils can be arranged to maximize the SNR (image quality) as well as the interventional access.

SUMMARY

The present invention is directed to a comfortable and open, adjustable, and/or pliable head coil assembly. The pliable surface coil assembly includes a flexible support and imaging coils wearable by, or placed against, a patient's head for scanning by an MRI. The flexible support of the surface coil assembly has an open framework that provides virtually unlimited access to the skull in order to provide surgical access, or to accommodate surgical or therapeutic navigational guides, ultrasound transducers, or other medical devices and peripheral equipment. The open framework of the flexible support permits surgical and therapeutic devices to be placed flush against the skull or cranium. Similarly, the flexible support can also be placed flush against the skull during scanning, and/or during interventional or therapeutic procedures. The openness and adjustability of the present invention enables the surgical or therapeutic devices to be placed flush with the skull or cranium simultaneously with the radiofrequency receiver antennae of the MRI coils also being flush with the skull.

The adjustable or pliable surface coil assembly also includes one or more sensors that are removably connectable to the support to measure electroencephalography EEG, electromyography EMG, electronystagmography ENG readings, and the like.

The adjustable or pliable surface coil assembly includes one or more soft, pliable coils that can be individually, or as a group, arranged on the patient to accommodate the support of diagnostic, interventional, or therapeutic applications. These multiple coils can be removably or permanently connected to a converter or connector device that then communicates, assimilates, or connects with the MRI scanner.

The above summary is not intended to limit the scope of the invention, or describe each embodiment, aspect, implementation, feature, or advantage of the invention. The detailed technology and preferred embodiments for the subject invention are described in the following paragraphs accompanying the appended drawings for people skilled in this field to well appreciate the features of the claimed invention. It is understood that the features mentioned hereinbefore, and those to be commented on hereinafter, may be used not only in the specified combinations, but also in other combinations or in isolation, without departing from the scope of the present invention.

Figure 1A:
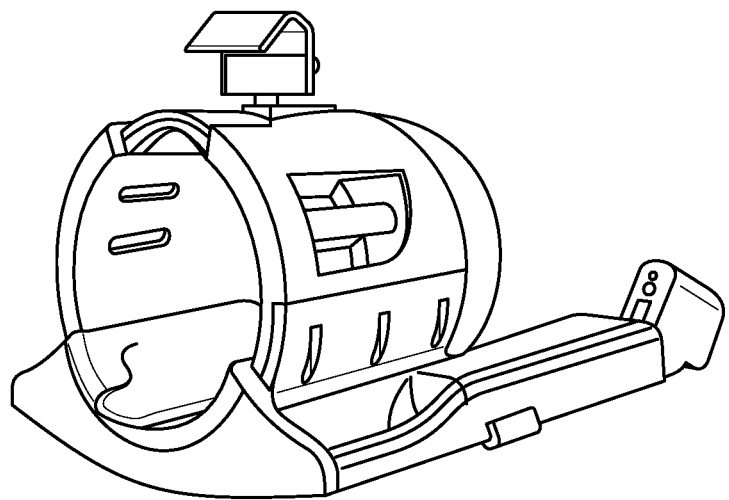
FIG. 1A is a perspective view of a conventional rigid non-wearable head coil.
Figure 1B:
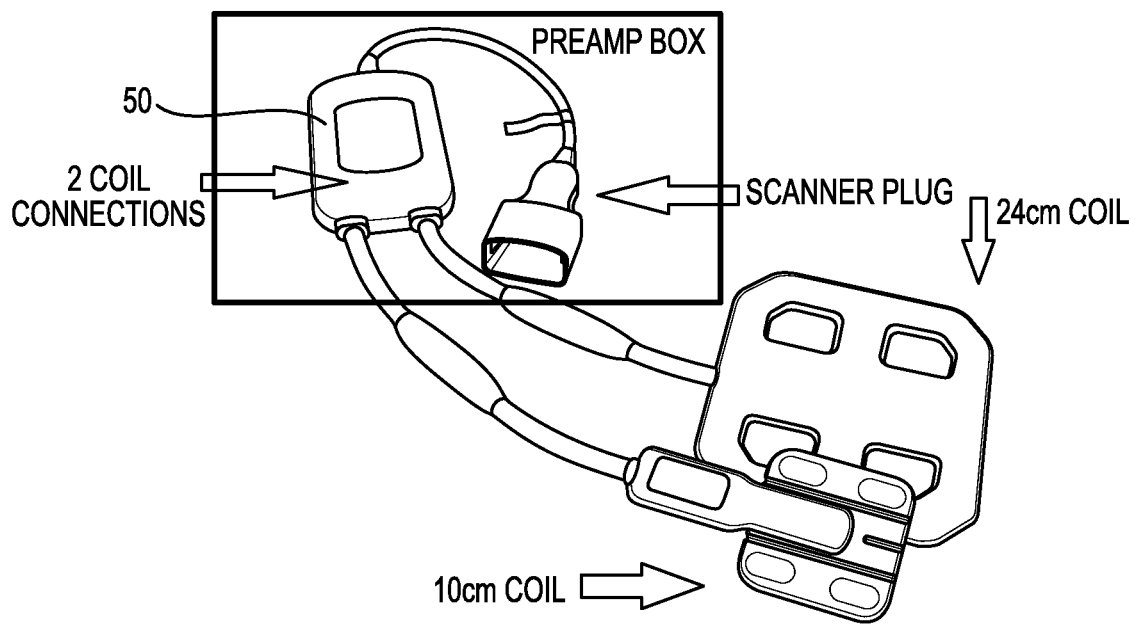
FIG. 1B is a perspective view of a preamp (signal amplifier) assembly that can be used with the wearable open and adjustable head coil system of the present invention.
Figure 2A:
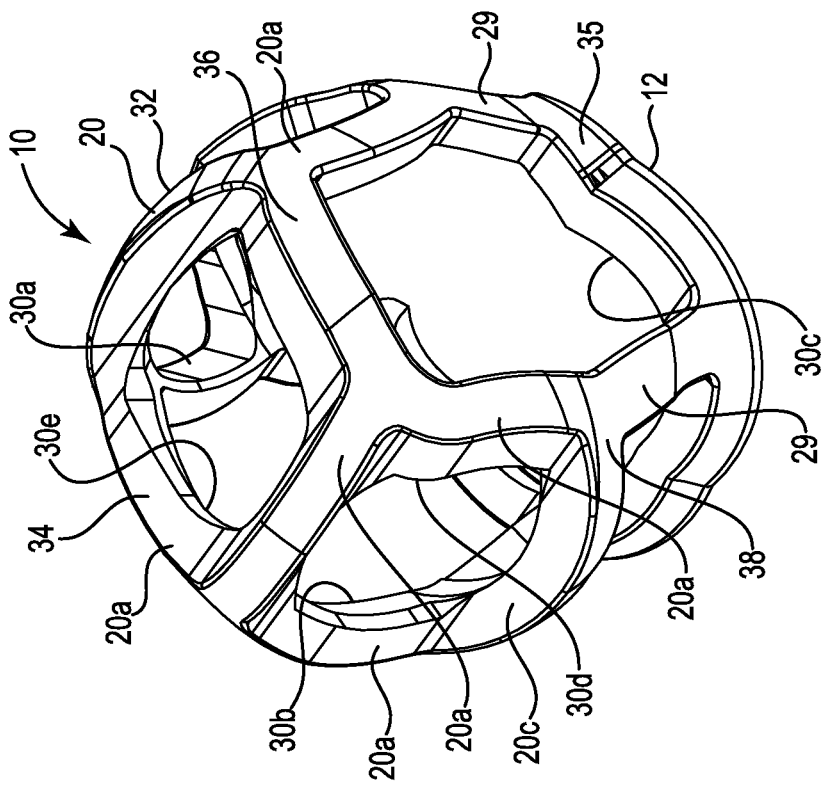
FIG. 2A is a front perspective view of a wearable open and adjustable head coil, according to an example embodiment of the present invention.
Figure 2B:
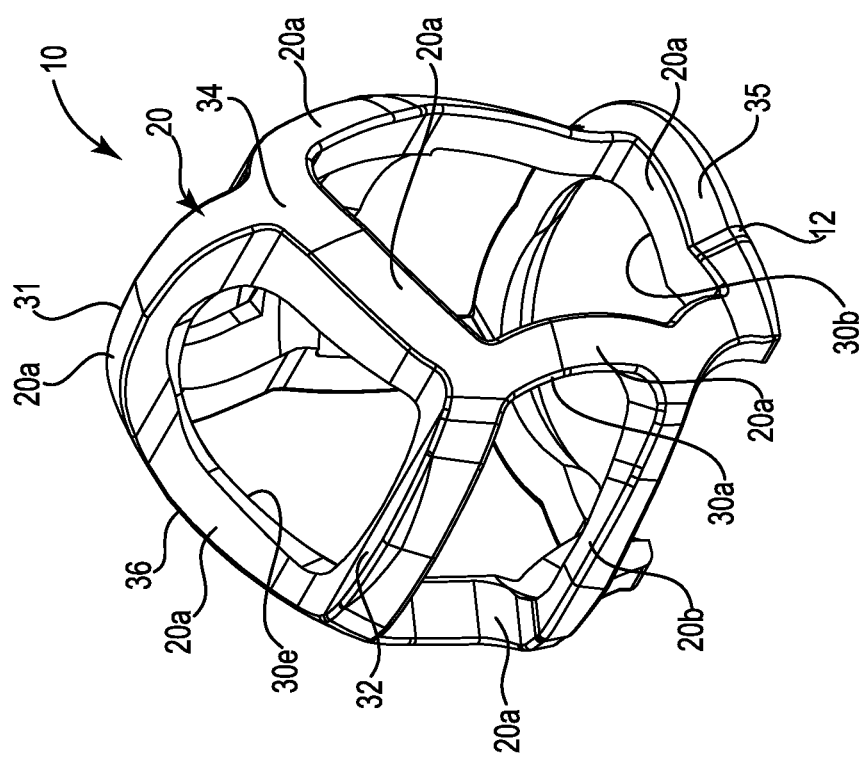
FIG. 2B is a rear perspective view of a wearable open and adjustable head coil, according to an example embodiment of the present invention.
Figure 2D:
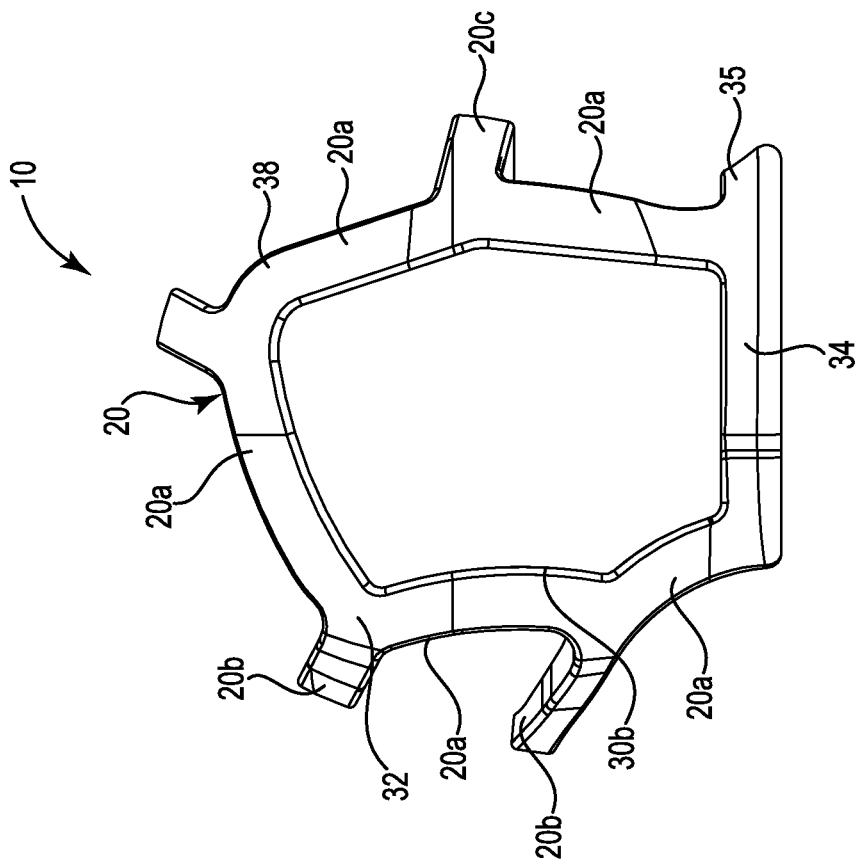
FIG. 2D is a second side view of a wearable open and adjustable head coil, according to an example embodiment of the present invention.
Figure 2C:
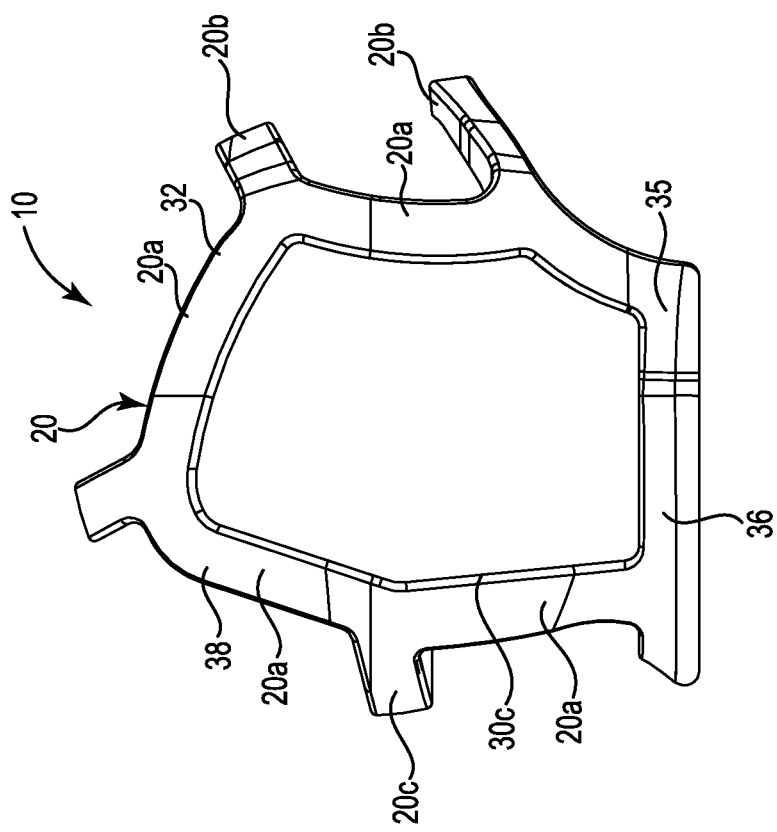
FIG. 2C is a first side view of a wearable open and adjustable head coil, according to an example embodiment of the present invention.

While the invention is amenable to various modifications and alternative forms, specifics thereof have been shown by way of example in the drawings and will be described in detail. It should be understood, however, that the intention is not to limit the invention to the particular example embodiments described. To the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration, rather than to limit the present invention.

Dimensions and relative proportions of components are merely provided as examples and can be varied unless specifically limited in a given claim. Thus, the dimensions and proportions can vary without departing from the scope of the invention.

As illustrated in FIGS. 2A-10C, the present invention comprises an open, adjustable, and/or pliable head or surface coil system 10 that includes a form fitting head coil 12 that is connectable to, and in communication with, a Magnetic Resonance Imaging ("MRI") device used for scanning a patient or subject. The various embodiments of the present invention generally include a head coil 12 that includes a support assembly 20 that can be comfortably worn on a patient's head. The support assembly 20 of head coil 12 supports MRI imaging coils 40. Unlike conventional head coils, the support assembly 20 of the present invention is comfortable, open, adjustable, and may be worn against or flush with a patient's head or body.

While the support assembly 20 is flush with the patient's body or head, the open and adjustable characteristics of the support assembly 20 enables diagnostic, therapeutic, and interventional devices—such as ultrasound transducers 60, drills, cannulas, and other sensors and medical devices such as electroencephalography EEG, electromyography EMG, or electronystagmography ENG sensors—to also be placed flush against the body or skull.

In the various example embodiments of the present invention, the support assembly 20 of the head coil 12 may comprise an open or closed cell foam material that is generally flexible and compressible to enable it to be moved or adjusted during scanning. The flexible and compressibility of the support assembly 20 also allows it to be adjusted during therapeutic or interventional procedures. Any material that provides cushioning, while also being flexible, may be used.

In yet another example embodiment of the present invention, the support assembly 20 of the head coil 12 may comprise any material(s) that encases or supports the radiofrequency receiver antennae of the MRI coils. For example, the support assembly 20 may comprise a generally thin and flexible substrate or band that can be bent and/or stretched to conform to a patient's head. The band configuration of the support assembly 20, and its adjustability, enables the radiofrequency receiver antennae and other imaging devices, such as ultrasound transducers, to simultaneously be placed flush with the patient's skull.

In one embodiment of the invention, the material is manufactured from a closed cell structure such that it can be sterilized by conventional sterilization processes to permit repeated use of the support assembly 20. In another example embodiment of the invention, the head coil 12 is designed such that it is easily disconnected from the MRI system. Further, the head coil 12 may be manufactured from materials that are recyclable. These innovative designs and materials enable the head coil 12 to be a single-use medical device item. The ability to disconnect and recycle a single-use head coil 12 is especially advantageous when it is used during interventional surgical procedures as it eliminates the requirement of sterilization.

As illustrated in the various figures, and as described in greater detail below, the support assembly 20 of the various embodiments may have a shape or configuration that can be placed upon, or worn by, a patient during scanning, surgical, and/or therapeutic procedures. The support assembly 20 includes a number of holes or openings that act as ventilation, or access openings for access to the patient's body or head. The openings also provide access for head holders or head fixation frames that include pins and/or clamps that contact the patient's head in order to stabilize it during an interventional procedure, such as cranial surgery. The openness and flexibility of the support assembly 20 enables surgeons and hospital staff to select the ideal location for securing the head holder to the patient's head, and provides a preferred option for nearly every patient head shape and size.

The openness and flexibility created by the openings of the support assembly 20 of the various embodiments also provide a surgeon and surgery staff with access to surgical or therapy site. The openings may be shaped and sized such that they are capable of accommodating medical devices, such as an ultrasound transducer (such as, for example, low intensity focus ultrasound ("LIFU") or high intensity focus ultrasound ("HIFU")). The support assembly 20 may also support other types of medical devices used during therapy, surgical, and other interventional procedures, including a cannula guide, lasers and deep brain stimulation (DBS) probes, etc.

Open Framework Headcoil

As shown in FIGS. 2A-4C, embodiments of a head coil 12 and support assembly 20 can be constructed of one or more framework support elements or members 20a that are configured to conform to a patient's head, and essentially 100% of the patient population. The elements 20a define an adjustable or pliable head coil system with a plurality of openings: anterior or face opening 30a, first side opening 30b, second side opening 30c, posterior opening 30d, and crown opening 30e. Like with other embodiments, the support assembly 20 of the head coil 12 provides support and comfort to a patient's head while also supporting or housing the MRI radiofrequency receiver antennae or imaging coils 40, ultrasound transducers 60, and other sensors and medical devices such as electroencephalography EEG, electromyography EMG, electronystagmography ENG sensors, and the like. The radiofrequency receiver antennae or imaging coils 40 can be enshrouded within, molded, or otherwise formed within support members 20a—e.g., sandwiched between two halves of the support members 20a.

Figure 3B:
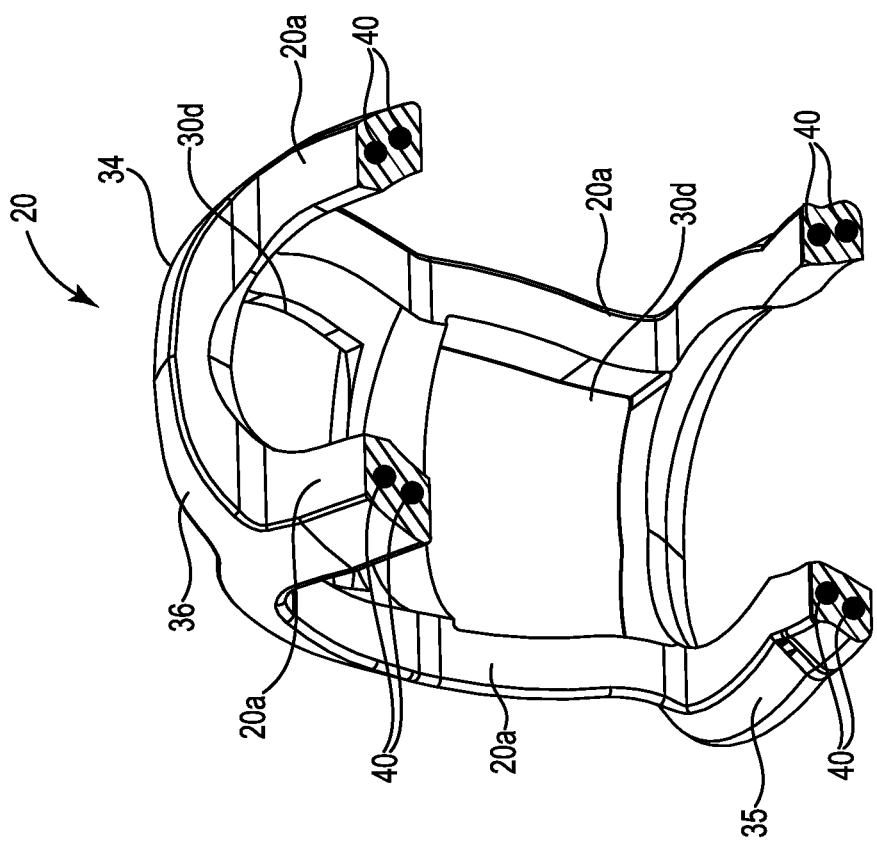
FIG. 3B is a cross section view of a wearable open and adjustable head coil, according to an example embodiment of the present invention.
Figure 3A:
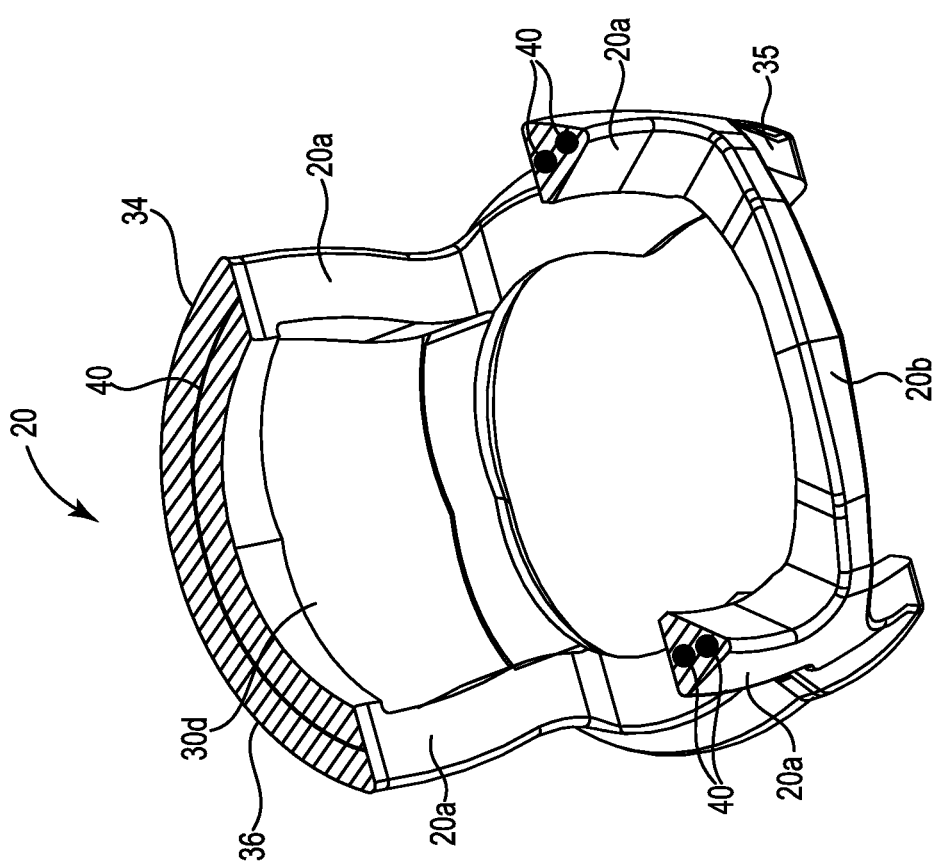
FIG. 3A is a cross section view of a wearable open and adjustable head coil, according to an example embodiment of the present invention.

As illustrated in FIGS. 3A and 3B, in order to capture the imaging, the support assembly 20 houses or otherwise includes the one or more radiofrequency receiver antennae or imaging coils 40. The radiofrequency receiver antennae or imaging coils 40 receive the radio frequency signal from the patient and then transmit the signals to a connected MRI control system for image processing. The radiofrequency receiver antennae or imaging coils 40 can be fixed, removably attached, or otherwise provided within or about portions of the framework members 20a and other portions of the support assembly 20.

Figure 4A:
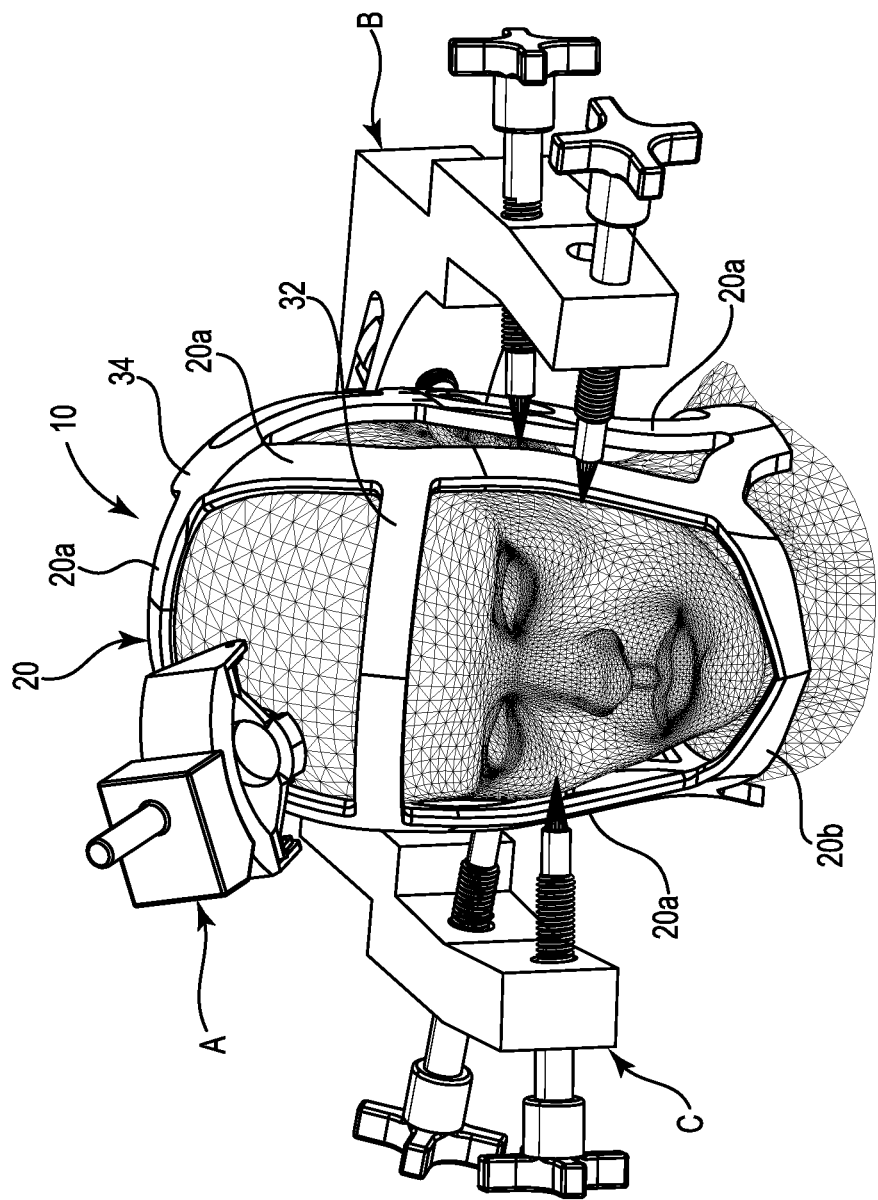
FIG. 4A is a perspective view of a wearable open and adjustable head coil used with a head holder and interventional tools, according to an example embodiment of the present invention.
Figure 4C:
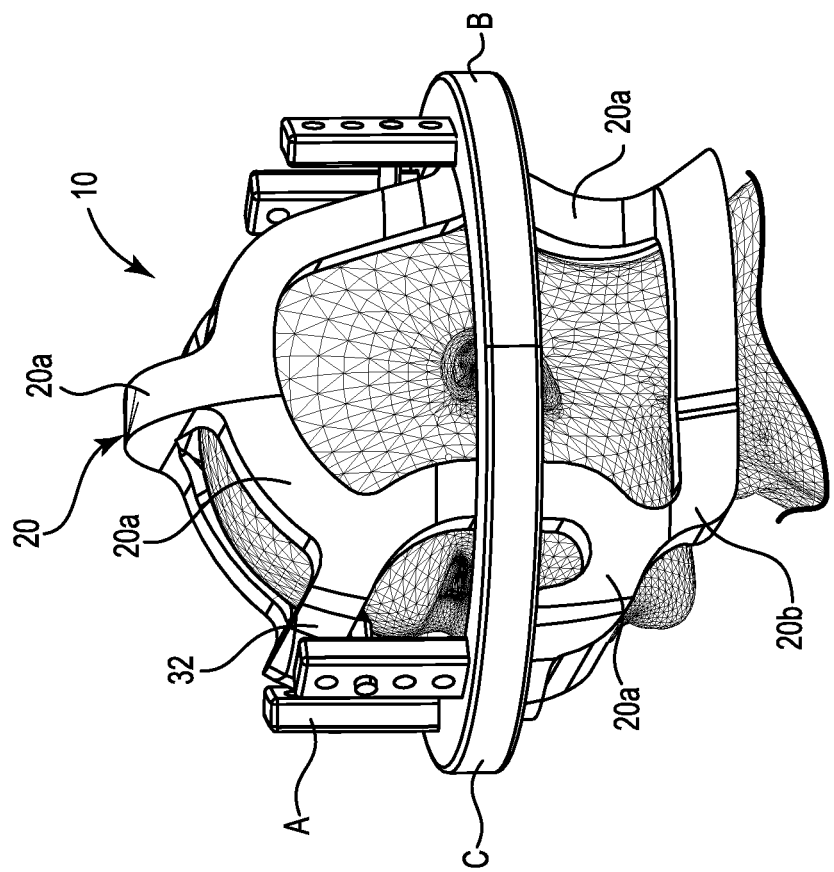
FIG. 4C is a perspective view of a wearable open and adjustable head coil used with a head holder, according to an example embodiment of the present invention.
Figure 4B:
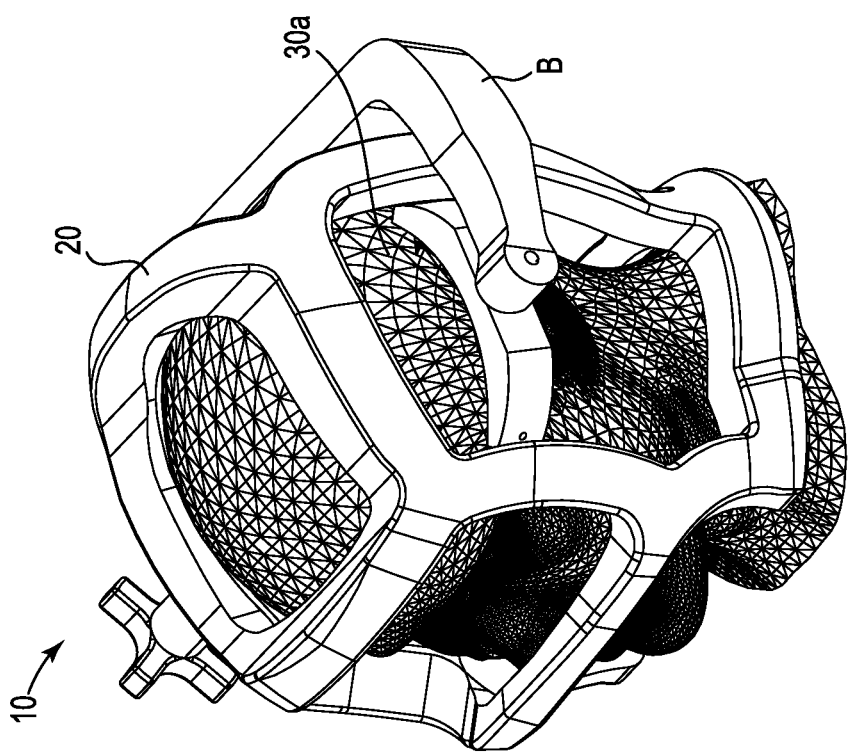
FIG. 4B is a perspective view of a wearable open and adjustable head coil used with a head holder, according to an example embodiment of the present invention.
Figure 5B:
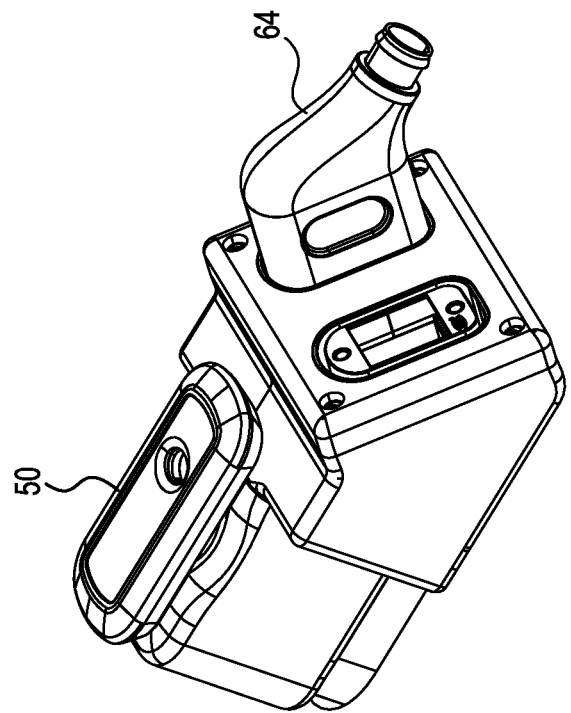
FIGS. 5A-5D are perspective views of a hub/preamp used for receiving and transmitting data between the wearable open and adjustable head coil and an MRI, according to an example embodiment of the present invention.
Figure 5A:
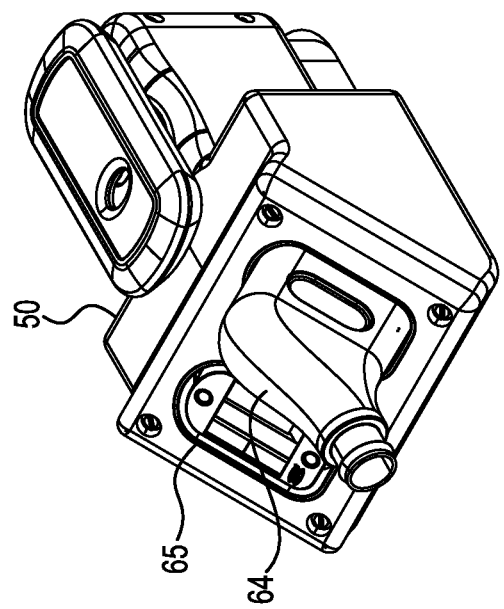
Figure 5D:
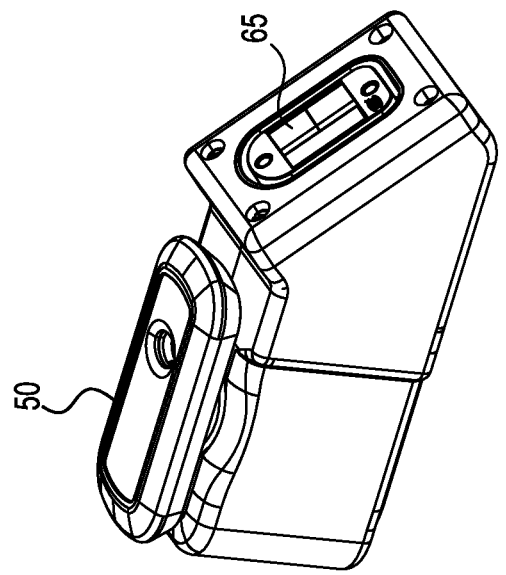
Figure 5C:
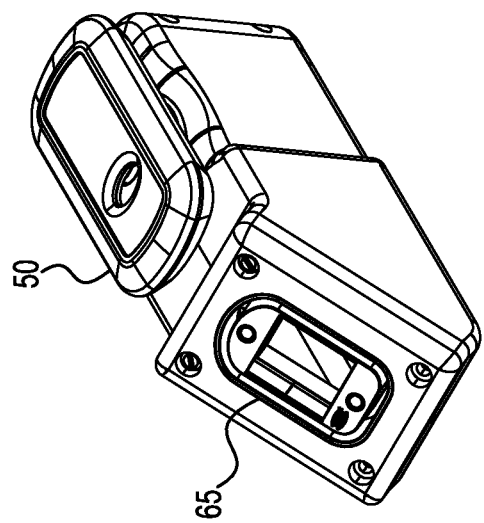

The overall support assembly 20 construct, including the individual framework members 20a, may be constructed in a shape or configuration to facilitate placement upon or around a patient during scanning, surgical, and/or therapeutic procedures (e.g., FIGS. 4A-4C). The members 20a can be generally arcuate, curvilinear, linear, angular, or they can take on a myriad of other shape configurations. In addition, the framework members 20a can be, as mentioned above, constructed of a cell foam material (open or closed), a generally thin flexible band, or other acceptably adjustable and pliable materials such that the support assembly 20 is generally flexible and/or compressible to enable it to be selectively formed around a patient's head, and to facilitate the described connectivity and use.

As particularly illustrated in FIGS. 2A-3B, the open framework head coil 12 embodiment may include a base portion 35 that extends generally around a back or posterior portion of a subject's head. Upright portions 29 can extend generally upward from the base portion 35. A face member 20b may extend generally across a pair of upright portions 29 and may span across a portion of a subject's face when worn. Similarly, the support assembly 20 may also include a rear member 20c that can extend generally across a posterior portion of a subject's head when worn. A crown portion 31 can span across the crown of a subject's head and can be connected to a left portion 34 and a right portion 36, also spanning generally proximate to the crown of a subject's head. Other portions or members can be included with the support assembly 20, and can include the radiofrequency receiver antennae, imaging coils 40, devices, and mechanisms disclosed herein.

In one example embodiment of the open framework head coil, the face member 20b can be one or two free ends, or edges, such that it can be bent, flexed away from, or completely removed from the head coil 12 and a subject or patient's head. The adjustability of the face member 20 enables the head coil 12 to be adjusted for patients with varying sized craniums. Its adjustability and removal also enable patients to feel less claustrophobic during a procedure. Fasteners, such as hook and loop fasteners can be used to secure ends of the face member 20b, or even portions of other members 20a, to a portion of the upright portions 29. It is envisioned that other fasteners and mechanisms can be employed to provide securement, such as snap features, temporary adhesives, clip or catch mechanisms, and the like.

It should be noted that any of the portions or members may be detachable or removable from the head coil 12. In this particular embodiment, contact or engagement surfaces can form a part of the head coil 12 to enable continuity between the radiofrequency receiver antennae or imaging coils 40 and communication with a hub and/or MRI device. The contact or engagement surfaces can comprise any material that is capable of connecting ends or portions of the radiofrequency receiver antennae or imaging coils 40 together and may be connected to, or formed as part of, the head coil 12.

The adjustability of the embodiments of the head coil 12 enable other medical devices and life supportive devices, such as ventilators, respirators, oxygen masks, tubes, catheters, electrodes, cervical collars, halos, probes, and other devices to be easily placed upon, or removed from, a patient. The ability to quickly and easily place or remove medical equipment while a patient undergoes diagnostic, therapeutic, and surgical procedures is a significant advantage over conventional birdcage head coils.

Turning now to FIGS. 4A-4C, and as described above, the openings 30a, 30b, 30c, 30d can act as ventilation and provide improved access to the subject or patient's head. As illustrated in FIGS. 4A-4C, the openings 30a, 30b, 30c, 30d can also provide access for surgical tools A, frames B, pins C, and other mechanisms and devices used to stabilize a patient's anatomy during an interventional procedure, as further detailed herein. The openings 30a, 30b, 30c, 30d are also adapted to receive any device used during therapy, surgical, and interventional procedures, such as an ultrasound device (e.g., a LIFU or HIFU device). Side openings 30b, 30c can also provide mechanical communication with the patient's temples or ears for placement of ultrasound transducers and other medical devices. The openings also provide access for the placement and removal of headphones, earbuds, or noise canceling headphones.

Again, while particular shapes, sizes, and locations of the openings 30a, 30b, 30c, 30d and support elements 20a are depicted in the figures of the open framework embodiment, one skilled in the art will appreciate that the dimensions, shapes, and locations of the openings 30a, 30b, 30c, 30d, support elements 20a, and any other depicted or described elements or members, can vary and may be selected and defined based upon typical therapy or surgical sites, tool sizes, device sizes, and the like.

Figure 8:
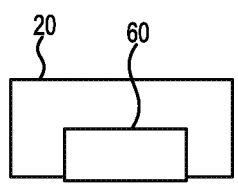
FIG. 8 is an edge view of a panel segment having at least one connector for connecting panel segments together, according to an example embodiment of the present invention.

The system 10 of the various embodiments can include one or more ultrasound transducers 60 (e.g., FUST transducers) mechanically integrated with the support assembly 20 and corresponding support members 20a—as particularly illustrated in FIG. 8. This allows for the placement of transducers 60, and the radiofrequency receiver antennae or imaging coils 40, generally flush to the patient's head, at the same time, and in the same plane. Further, transducers 60 can be repositioned in a myriad of locations on the patient's head due to the connectivity and attachment options of the support assembly 20. For instance, if the radiofrequency receiver antennae or imaging coils 40 is interfering with the placement of the focused transducer 60, the flexibility of the members 20a, the openings 30a, 30b, 30c, 30d, and the coil 40 permits and facilitates adaptive repositioning to allow for proper placement.

When used for interventional or therapeutic procedures, the support assembly 20 is applied to the patient prior to adding fixation or other hardware and devices. The support assembly 20 and the configuration of the support members 20a and openings 30a, 30b, 30c, 30d permits access to interventional hardware and test setups—e.g., cannula guides, head fixations, sterile draping, and the like. This, in turn, means that the support assembly 20 can interface with virtually all head fixation and connective devices. The support assembly 20, head fixation hardware, and interventional tools or devices can all touch the patient simultaneously with the radiofrequency receiver antennae or imaging coils 40.

System Hub

The system 10 of the various embodiments of the present invention can also include a hub 50 that is able to receive or connect various imaging coils, including the imaging coils of the head coil 12. The radiofrequency receiver antennae or imaging coils 40 are bundled together into a plug or plugs 64 that connect to an external hub or preamp 50 (as illustrated in FIGS. 5A-5D) that interface or communicates with the MRI scanner. The hub 50 can have one or more sockets or receivers 52 to receive a number of different surface coil plugs, adapters, and the like. In one example embodiment of the invention, the hub 50 can accommodate any number of channels. For instance, 1 to 48 channels may be used that enable it to connect with the support assembly 20 and other imaging devices, such as a 24 cm surface coil, a 10 cm surface coil, a posterior surface coil, a spine surface coil, a face surface coil (discussed below), etc. The number of channels provided are merely exemplary and any number of channels are possible and are considered to be within the spirit and scope of the invention.

Open-Face Head Coil

Turning now to FIGS. 6A-6E, the head coil 12 of the present invention may have a generally open face, and/or include various openings. The open-face head coil 12 embodiment, like the other embodiments, is manufactured from a comfortable material and is designed to position the radiofrequency receiver antennae or imaging coils 40 flush against the surface of a subject or patient's head.

In one example embodiment of the open-face head coil 12, the support assembly 20 also includes generally opposed ear or temple holes or openings 24*a* and 24*b,* on each side of the support assembly 20. The ear or temple holes or openings 24*a* and 24*b* are sized and shaped to receive any device used during therapy, surgical, and interventional procedures. For instance, as described above, LIFU or HIFU devices may be placed next to a temple or lateral cranial surface to conduct ultrasound imaging. Other devices, such as headphones or noise canceling headphones, may also be inserted into or placed on the ear or temple openings 24*a* or 24*b*. As described above, patient stabilization devices, including head stabilization or holders, may also utilize the ear or temple openings 24*a* or 24*b*.

Figure 6A:
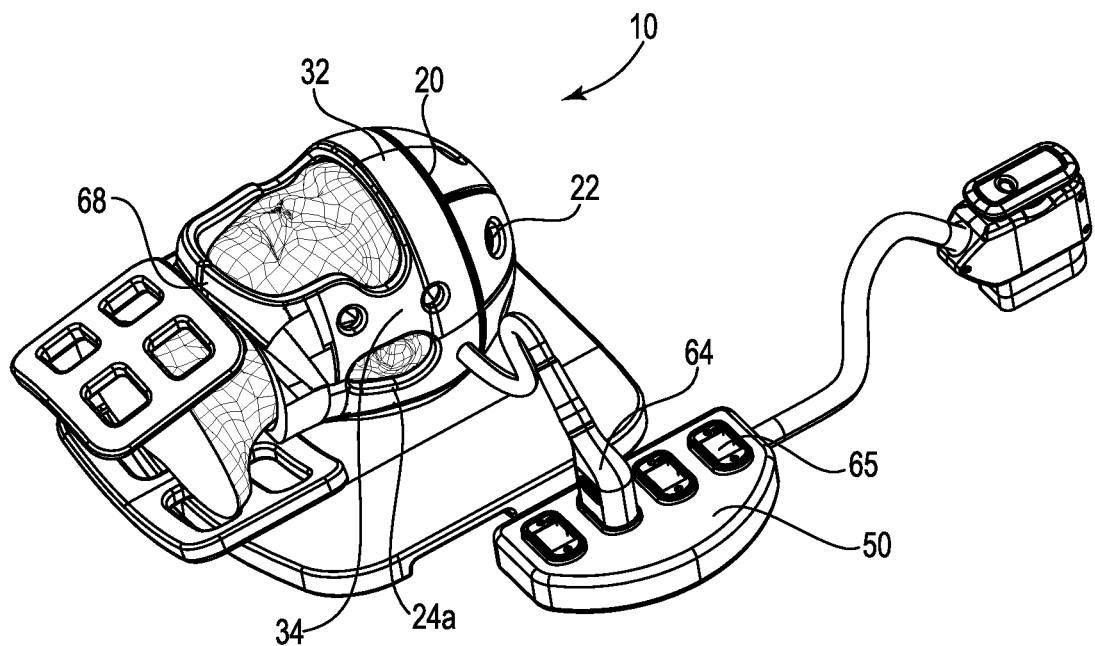
FIG. 6A is a perspective view of a wearable open and adjustable head coil connected to a hub/preamp used for receiving and transmitting data between the head coil and an MRI, according to an example embodiment of the present invention.
Figure 6B:
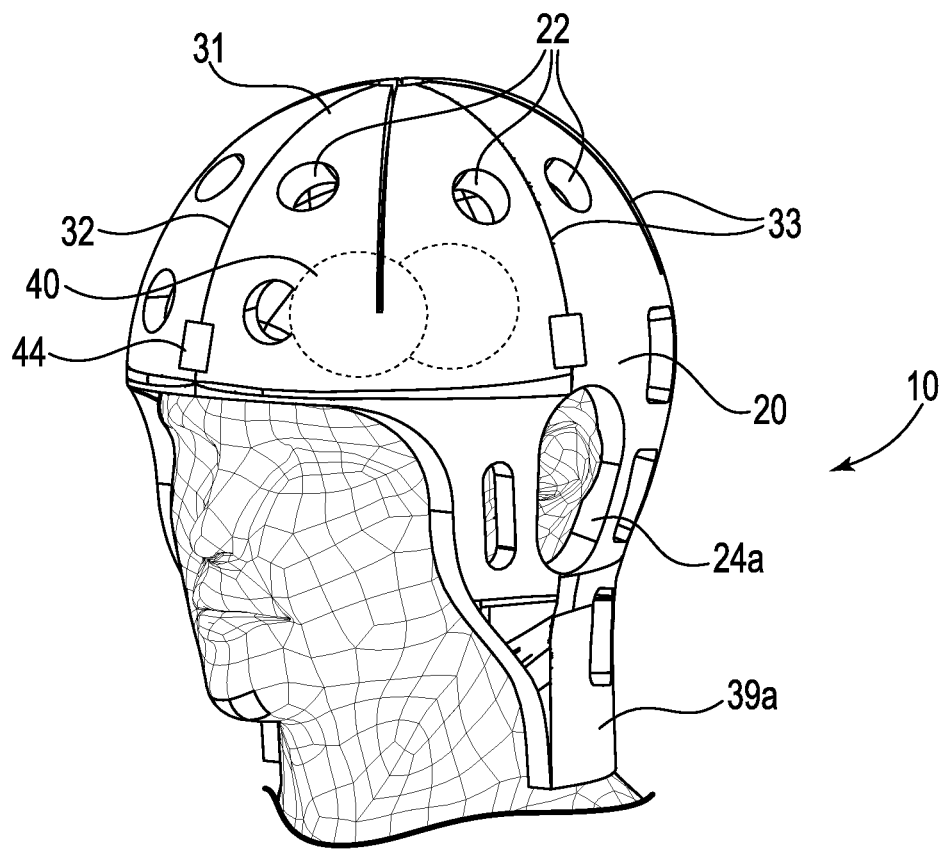
FIG. 6B is a perspective view of a wearable open and adjustable head coil system, according to an example embodiment of the present invention.
Figure 6C:
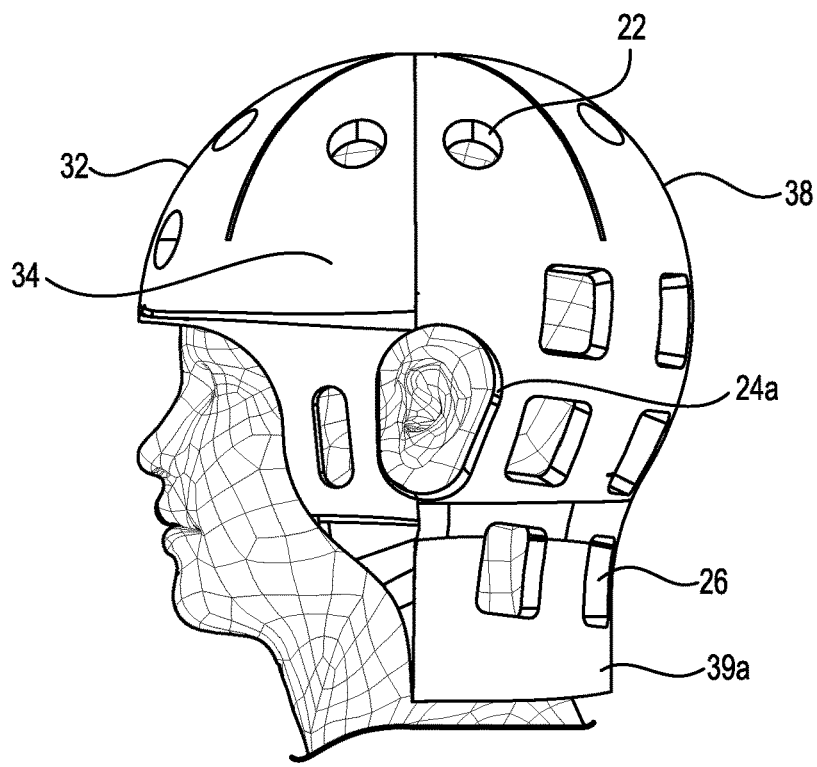
FIG. 6C is a side view of a wearable open and adjustable head coil system, according to an example embodiment of the present invention.
Figure 6D:
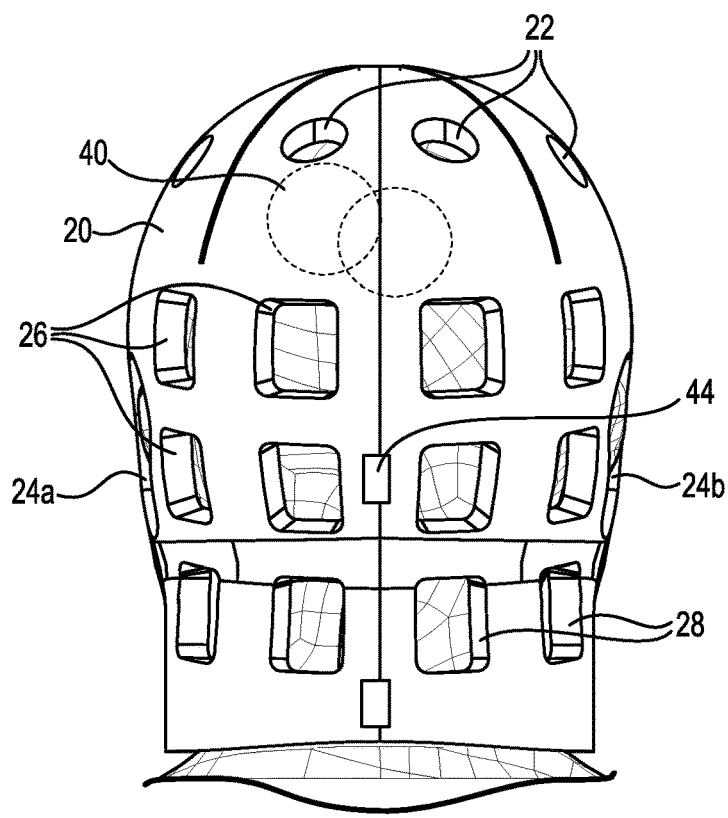
FIG. 6D is a view of a wearable open and adjustable head coil system, according to an example embodiment of the present invention.

As illustrated in FIGS. 6C and 6D, the support assembly 20 may include other openings, such as one or more posterior or rear holes or openings 26. Similar to the ear or temple openings 24*a* and 24*b*, the rear openings 26 may also be utilized for ventilation and patient stabilization, including head stabilization, and therapy or surgical site access. The rear or posterior openings 26 may be spaced generally apart from each other and may be positioned such that they span across a rear of the support assembly 20. The rear openings 26 may also have a shape and size capable of accommodating ultrasound transducers and other medical devices that may be used during therapy, surgical, or other interventional procedures.

As further illustrated in FIG. 6D, the support assembly 20, for use on a patient's head, may also include a number of cervical or neck holes or openings 28. The openings 28 can be formed and extend through a rear or side of the support assembly 20. Similar to other holes and openings, the cervical openings 28 provide ventilation, stabilization, and therapy or surgical site access. The cervical openings 28 are generally spaced apart and span across an axis transverse to a longitudinal axis of the support assembly 20. The cervical openings 28 may also have a shape and size capable of accommodating ultrasound devices (such as LIFU HIFU) and other medical devices that may be used during therapy, surgical, or other interventional procedures.

Although a particular shape, size, and location of openings 22, 24*a* and 24*b,* 26, and 28 are illustrated, one skilled in the art will appreciate that the dimensions and locations of openings 22, 24*a* and 24*b,* 26, and 28 may vary and may be selected based upon typical therapy or surgical sites, tool sizes, and the like. Therefore, the illustrations should not be considered limiting.

Open-Face/Flap-Access Head Coil

In another example of the open face embodiments of FIGS. 6A-6E, the support assembly 20 may include a top or crown portion 31 having one or more flaps 33 that may be folded, bent, or moved away from a surface of a patient. For example, it can be moved away from the top of a patient's body or head in order to permit access for examination or surgery. The flaps 33 are capable of continuing to receive MRI radiofrequency signals during flexing, movement, and transmitting signals to the MRI control system, including the reception of radiofrequency signals being emitted by a cannula guide or other apparatus. The ability to continue receiving radiofrequency signals enables continuous imaging during therapy, surgical, or other interventional procedures.

In yet another example embodiment, the material of the support assembly 20 formed around the openings 22, 24*a* and 24*b,* 26, and 28 may comprise a more elastic or compressible material that enables the openings 22, 24*a* and 24*b,* 26, and 28 to be moved, reshaped, or opened wider for increasing access to various portions of the patient, including the patient's head. The adjustability of the openings 22, 24*a* and 24*b,* 26, and 28, and flaps 33 (as well as openings in other embodiments), enables the support assembly 20 to accommodate different stabilizers, LIFUs, HIFUs, and other sensors used during therapy, surgery, or other interventional and therapeutic procedures.

Wrap Head Coil

In yet another example embodiment of the invention, as illustrated in FIGS. 9A-9E, the support assembly 20 may have a number of flexible portions or panels 32, 34, 36, 38, 39*a* and 39*b* that can be wrapped around or conformed to a patient's body or head. The portions or panels 32, 34, 36, 38, 39*a* and 39*b* may be integrally formed together by being connected by a living hinge, a bridge, a web material, etc. The hinge or bridge material may comprise the same material as the support assembly 20, but may be generally thinner to allow it to more easily bend or flex.

In another embodiment of the invention, a coupler or like mechanism may be used to connect the portions or panels 32, 34, 36, 38, 39*a* and 39*b* together. The coupler may comprise a generally elastic web material such as nylon, or a similar webbing material, connected to and extending between the portions or panels 32, 34, 36, 38, 39*a* and 39*b*. The webbing material can also facilitate ventilation between the portions or panels 32, 34, 36, 38, 39*a* and 39*b*. It can further enable the portions or panels 32, 34, 36, 38, 39*a* and 39*b* to separate away from each other to accommodate patients with varying sized and shaped anatomy and heads. Any material that stretches, and will permit expansion of the portions or panels 32, 34, 36, 38, 39*a* and 39*b* or support assembly 20, may be utilized.

Figure 9A:
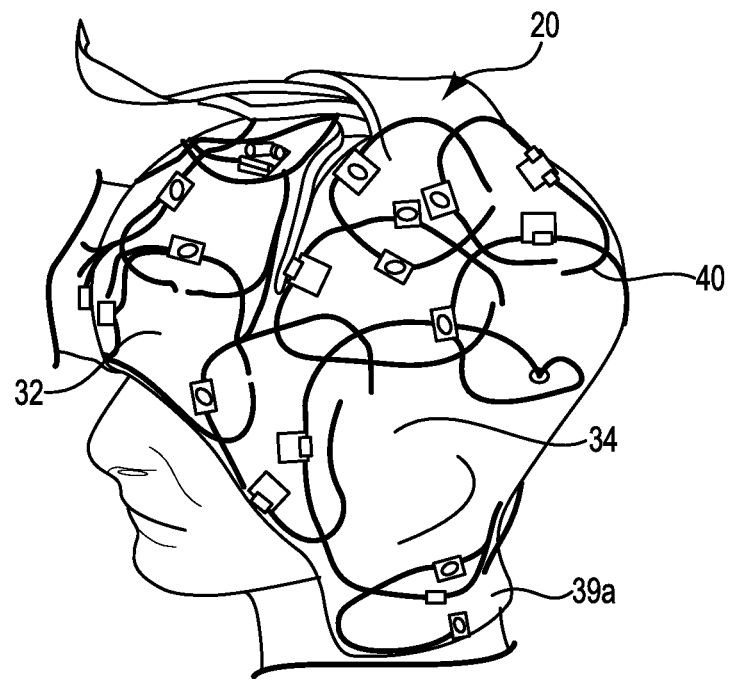
FIG. 9A is a left perspective view of wearable open and adjustable head coil panels, according to an example embodiment of the present invention.
Figure 9B:
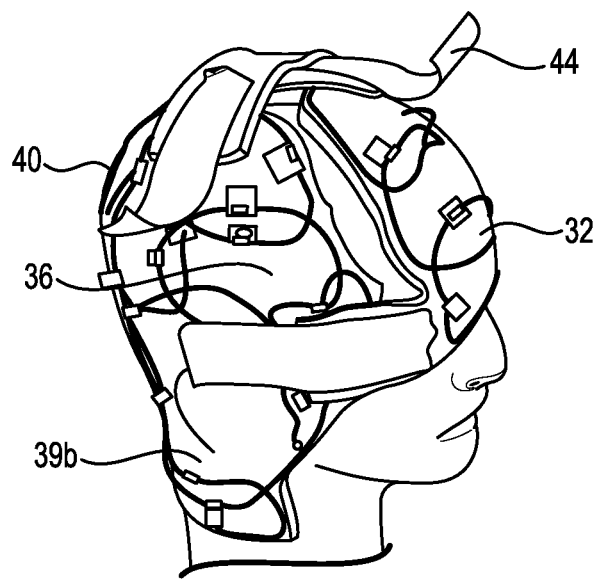
FIG. 9B is a right perspective view of wearable open and adjustable head coil panels, according to an example embodiment of the present invention.

As illustrated in FIG. 9A, the portions or panels 32, 34, 36, 38, 39*a* and 39*b* may be separate individual panels having undulating peripheral edges that can be removably positioned next to or near a corresponding shape of another respective portion or panel 32, 34, 36, 38, 39*a* and 39*b*. The portions or panels 32, 34, 36, 38, 39*a* and 39*b* may have varying undulations along their peripheral edges. For instance, one or more of the portions or panels 32, 34, 36, 38, 39*a* and 39*b* may have greater peripheral undulations such that they resemble a starfish or sea urchin.

In one embodiment of the invention, the portions or panels 32, 34, 36, 38, 39*a* and 39*b* may be connected together by a coupler or fastener 44, such as a hook and loop fastener, a snap or clip feature, and the like. The coupler 44 may be disposed on the edges of the panels 32, 34, 36, 38, 39*a* and 39*b* in order to removably connect the edges to one another. In yet another example embodiment of the invention, the fasteners or couplers 44 may extend between and connect to outer surfaces, or inner surfaces, of the panels 32, 34, 36, 38, 39*a* and 39*b*.

In still another embodiment of the invention, an expanding securement member, such as a nylon stocking cap, may be fit onto a patient's body or head such that each separate portion or panel 32, 34, 36, 38, 39*a* and 39*b* may be removably attached or connected to the expanding securement member by a coupler or fastener (such as a hook and loop fastener). The expanding securement member and the shape of the separate portions or panels 32, 34, 36, 38, 39a and 39b permits a user to position the portions or panels 32, 34, 36, 38, 39a and 39b around a stabilizer, such as a head frame immobilizing a patient's head. It also permits a user to place the portions or panels 32, 34, 36, 38, 39a and 39b in any desired location on a patient's body. The ability to remove or reposition the separate portions or panels 32, 34, 36, 38, 39a and 39b on the expanding securement member enables more flexibility in capturing desired images. The ability to remove or reposition the separate portions or panels 32, 34, 36, 38, 39a and 39b also provides greater flexibility in accessing desired therapy or surgical sites.

The portions or panels 32, 34, 36, and 38 can differ depending upon the scanning, therapy, or surgical needs, but generally may include a front portion or panel 32 that is positionable against or flush with a patient's frons or forehead. It can also include a first or left portion or panel 34, and a second or right portion or panel 36, that are positionable against or flush with the left and right temples or sides of a patient's head. The front portion or panel 32 may be connected to the left portion or panel 34, or the right portion or panel 36. The left portion or panel 34 and the right portion or panel 36 may be connected by at least one posterior or rear portion or panel 38 that can be positioned against or flush with a posterior or back of a patient's head.

Figure 9C:
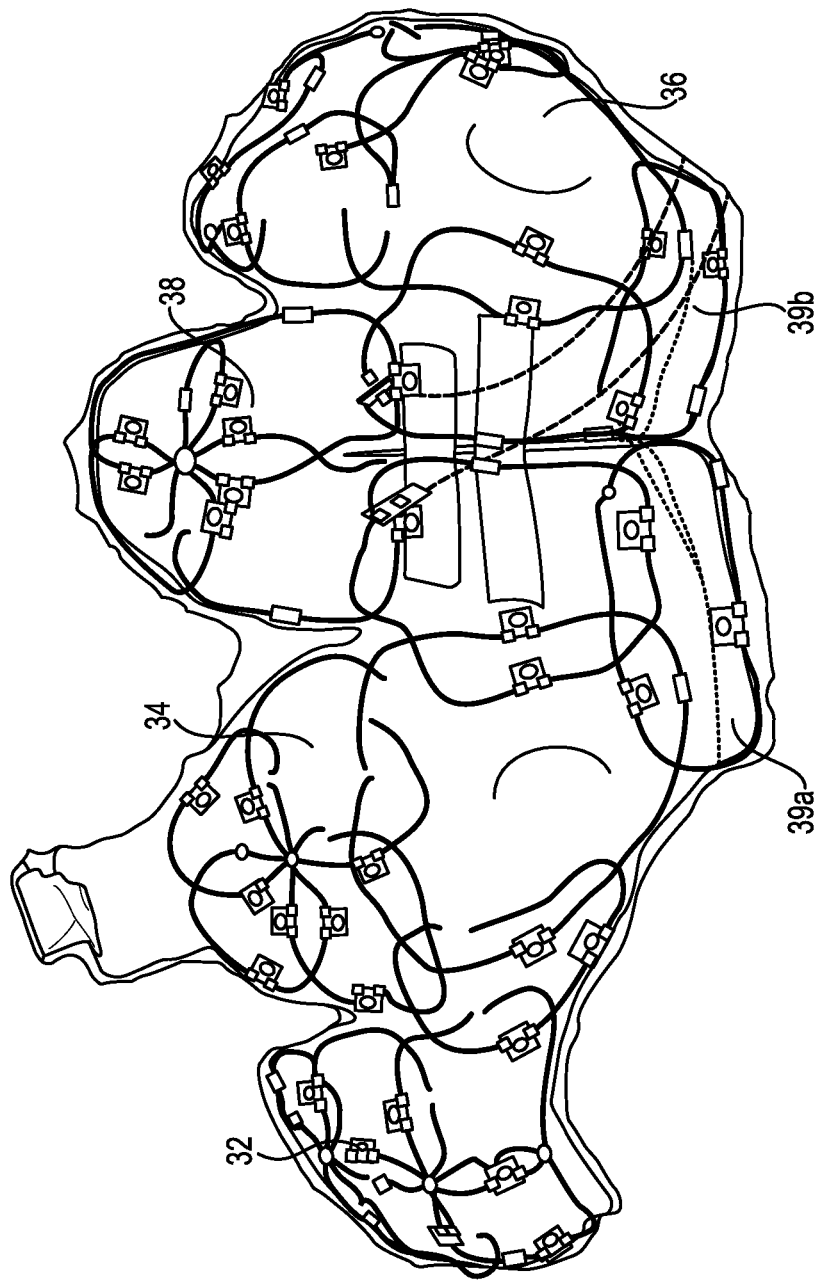
FIG. 9C is a top view of wearable open and adjustable head coil panels, according to an example embodiment of the present invention.
Figure 9D:
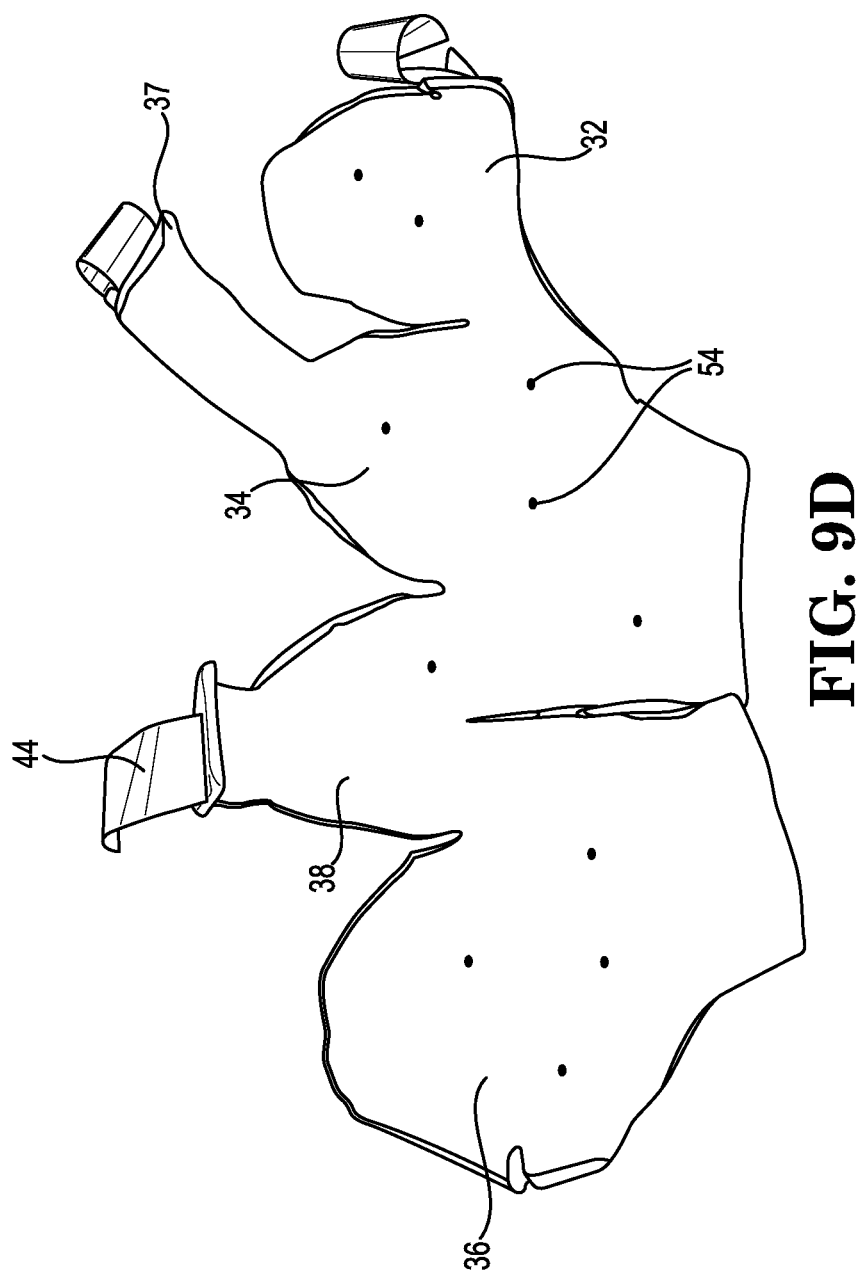
FIG. 9D is a perspective view of wearable open and adjustable head coil panels, according to an example embodiment of the present invention.

As with the open-face head coil, and as illustrated in FIGS. 9C and 9D, one or more of the portions or panels 32, 34, 36, and 38 of the wrap head coil may have one or more crown flaps 37 that extend from a portion of the panels 32, 34, 36, and 38 to cover at least a portion of a crown of a patient's head. The crown flaps 37 may be manufactured from a similar or dissimilar material to the support assembly 20. Similar to other head coil embodiments of the present invention, couplers or fasteners 44 may be coupled to the crown flaps 37 to enable coupling of the crown flaps 37 to the other panels 32, 34, 36, and 38.

Importantly, as with other head coil embodiments of the present invention, the crown flaps 37, any portions or panels, or any openings 22, 24a and 24b, 26, and 28 of the support assembly 20 may be used to provide access for a surgical cannula guide that is typically used during neurosurgery. The crown flaps 37, and panels and openings 22, 24a and 24b, 26, and 28, also provide access for other therapy or neurosurgery equipment such as forceps, hydrocephalus shunts, neuroendoscopy, implants, and aneurysm clips. The pivoting or movable connection between the individual portions or panels enable a physician or attendant to move or pivot a desired portion or panel in order to obtain access to a particular examination or surgical site. After one or more portions or panels are moved to enable access, it may be returned to its original location.

Again, similar to other head coil embodiments of the present invention, the support assembly 20 of the wrap head coil may include at least one or more neck portions or panels 39a and 39b. The neck panels 39a and 39b may be extensions of other panels, or may be individual panels that are coupled to, and extend away from, a lower portion or edge of the rear panel 38, the left panel 34, and/or the right panel 36. The neck panels 39a and 39b extend generally from a base of a patient's head toward their shoulders or back. The neck panels 39a and 39b also support receiver or imaging coils used for imaging portions of the neck of a patient.

Sensor, Imaging and Imaging Coil Support

The support assembly of the head coil 12 embodiments of the present invention is capable of supporting or housing the radiofrequency receiver antennae or imaging coils 40, and other types of sensors and imaging devices. As described above, in order to capture the scanned images, the support assembly 20 supports or houses one or more receiver or imaging coils 40. The radiofrequency receiver antennae or imaging coils 40 receive the radio frequency signal from the patient and then transmit them to a connected MRI control system for processing and image generation. As illustrated in FIGS. 3A-3B, 6B, 6D, 9A-9C, and 9E, the radiofrequency receiver antennae or imaging coils 40 may be fixed in, or removably attached to, an inner or outer surface of the support assembly 20. In one example embodiment, the radiofrequency receiver antennae or imaging coils 40 can be connected to one or more fasteners fixed to the surface of the support assembly 20. The fasteners may comprise clips, snaps, hook and loop devices, adhesives, and the like.

In another example embodiment of the invention, the inner or outer surface of the support assembly 20 includes grooves or channels formed therein that receive and hold or retain the radiofrequency receiver antennae or imaging coils 40. The receiver or imaging coils 40 may be removable from the fasteners or grooves for repair, replacement, or to isolate or remove a particular portion or panel of the support assembly 20.

As particularly illustrated in FIGS. 3A and 3B, the radiofrequency receiver antennae or imaging coils 40 can also be molded, formed, housed, or positioned within the support assembly 20. For instance, during the manufacturing process, the support assembly 20 may be formed around the radiofrequency receiver antennae or imaging coils 40. The support assembly 20 may also be 3D printed or thermalformed around the receiver or imaging coils 40. The receiver or imaging coils 40 may also contain, or may be in communication with, a circuit board that can be attached to or imbedded within the support assembly 20.

Figure 9E:
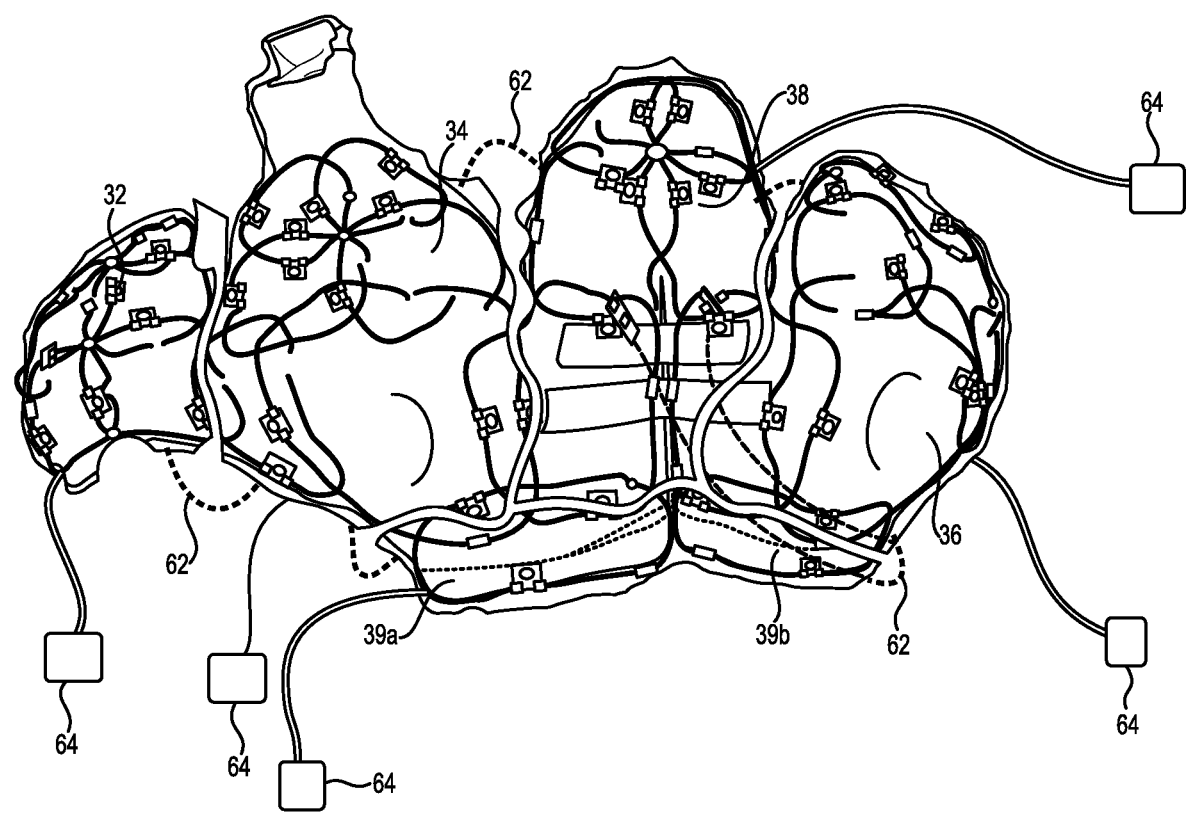
FIG. 9E is a perspective view of wearable open and adjustable head coil panels, according to an example embodiment of the present invention.

The radiofrequency receiver antennae or imaging coils 40 are comprised of a generally flexible material, such as a braided, stranded, or twisted wire, or other material capable of receiving radiofrequency signals, such as RF polymers. The flexibility of the imaging coils 40 enables the portions or individual panels to flex, pivot, or otherwise move. As illustrated in FIG. 9E, the portions or separate panels 32, 34, 36, 38, 39a and 39b, may be operatively coupled together by a patch or imaging coil connector 62. The imaging coil connectors 62 may be removably connected to, or plugged into, separate portions or panels 32, 34, 36, 38, 39a and 39b. The imaging coil connectors 62 may comprise the same material as the radiofrequency receiver antennae or imaging coils 40. Each of the panels 32, 34, 36, 38, 39a and 39b may include one or more receptacles disposed on its edge, or outer surface, to connect the imaging coil connectors 62 of the panels 32, 34, 36, 38, 39a and 39b together.

The support assembly 20 is manufactured having a thickness that positions the radiofrequency receiver antennae or imaging coils 40 a predefined distance from a patient. In one embodiment, the support assembly 20 has a thickness to position the imaging coils 40 either flush with, or a distance of approximately 5 mm from, the surface or skin of the patient. The distance of the radiofrequency receiver antennae or imaging coils 40 is designed to have a high signal-to-noise ratio, while still being safe for the patient. Greater or lesser MRI frequencies and/or MRI field strengths are possible and should be considered to be within the spirit and scope of the present invention. Additionally, RF polymers, which may be proven to be safe for patients, may be conformed to the head with little or no foamed structure.

In an example embodiment of the invention, for instance, the imaging coils 40 may be underlapped. The underlapping of the radiofrequency receiver antennae or imaging coils 40 may occur in some or all of the receiver or imaging coils 40. The support assembly 20 radiofrequency receiver antennae or imaging coils 40 can have six (6) channels, although the number of channels may be increased or decreased depending upon the particular need and application.

As illustrated in FIG. 8, any type of device (e.g., ultrasound devices 60) used or described herein may be incorporated or integrated into the material or structure of the support assembly 20. For instance, as described above, an ultrasound transducer (LIFU or HIFU) may be incorporated or integrated into a bottom or lower surface of the support assembly 20 to permit a user to perform ultrasound imaging without having to remove any of the portions or panels.

Figure 7A:
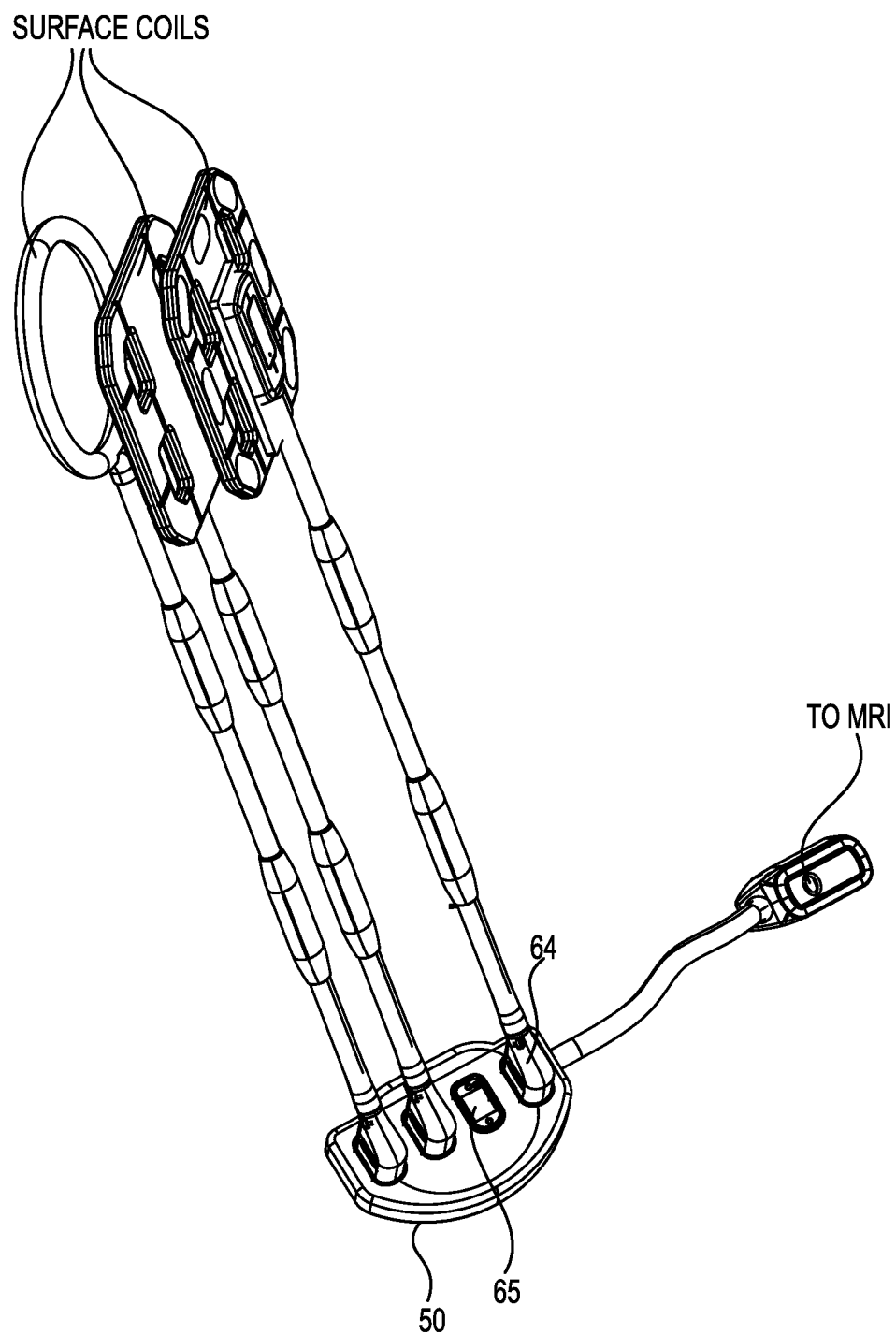
FIG. 7A is a perspective view of a preamp (signal amplifier) assembly having a plurality of connectors for connecting distinct coils, according to an example embodiment of the present invention.
Figure 7B:
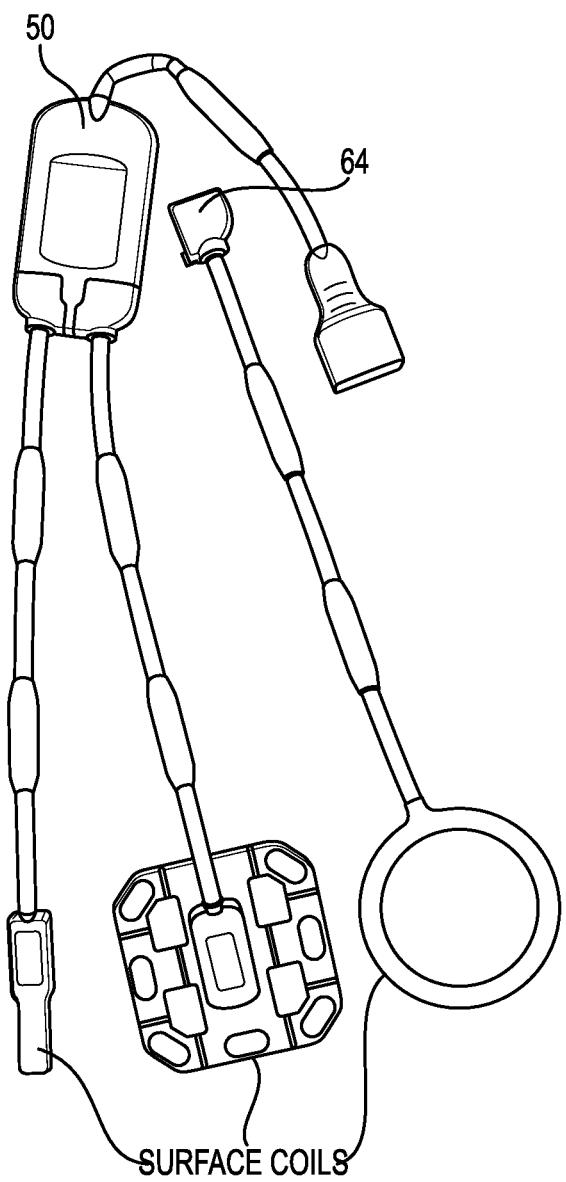
FIG. 7B is a top view of a preamp assembly having distinct coils, according to an example embodiment of the present invention.

Similar to the open framework head coil embodiment, and as illustrated in FIGS. 6A and 9E, each portion or separate panel 32, 34, 36, 38, 39*a* and 39*b* may have its own cable and plug 64 that may be removably connected to a corresponding receptacle 65 connected to or formed as part of the preamp (signal amplifier) 50. In another embodiment, each of the portions or panels 32, 34, 36, 38, 39*a* and 39*b* are operatively coupled together by, for instance, plugging into a hub that is then connected to a receptacle 65 of preamp (signal amplifier) 50. Various plug or connection configurations are possible and should be considered to be within the spirit and scope of the invention. Although FIGS. 7A-7B illustrate panels 32, 34, 36, and 38 as being connected to the preamp (signal amplifier) 50, it should be understood that any number of panels or surface coils may be connected to the preamp.

Figure 6E:
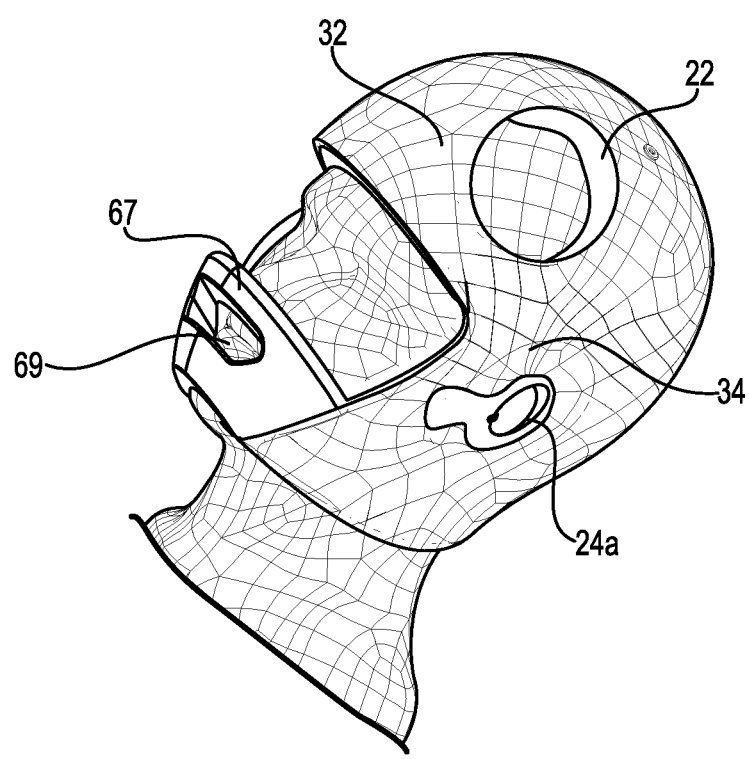
FIG. 6E is a perspective view of a wearable open and adjustable head coil system with an opening for an ultrasound transducer or other imaging devices, according to an example embodiment of the present invention.

Again, referring to FIGS. 7A-7B, the preamp (signal amplifier) 50 can also receive other devices or surface coils to expand the capabilities of the coil system 10. For example, as illustrated in FIGS. 6A and 6E, the adjustable or pliable surface coil assembly 20 of a head unit may include a face surface coil 67 or a chin surface coil 68, each having a number of channels. For instance, the face and chin surface coils 67 and 68 can each have at least 2 to 6 channels that are used to image the anterior aspects of a patient's head. The face and chin surface coils may also have more than 6 channels. The face surface coil 67 includes a support or base that is removably connectable or positionable proximate the support assembly 20. The face or chin surface coils also include one or more imaging coils 40 that are connected to, and are in communication with, the preamp 50. As illustrated in FIG. 6E, the face surface coil 67 may include one or more holes or openings 89 that permit a user or patient to more easily breathe and speak while undergoing a procedure.

In one embodiment of the invention, the base of the face surface coil has a contour that permits it to rest against a patient's face. The base may have one or more holes for ventilation, or to enable a patient to see and avoid any potential instances of claustrophobia or discomfort.

The adjustable surface coil assembly 20 may also include one or more sensors operatively coupled to, or positionable with respect to, the support assembly 20. The sensors may comprise electroencephalography EEG, electromyography EMG, or electronystagmography ENG sensors, although other sensors may also be used. In one embodiment, as illustrated in FIG. 9D, an inner surface of the surface coil assembly 20 or panels 32, 34, 36, and 38 may have indicia or marks 54 that may identify a sensor's location. The indicia 54 enables a practitioner to easily identify and place the sensors, and to relocate them in exact positions for later diagnostic, therapeutic, or interventional procedures.

In another embodiment, sensor fasteners may be connected to the inner surface of the support assembly 20 or panels 32, 34, 36, and 38 of the support assembly 20. The sensor fasteners may comprise snap fasteners, or other fasteners described herein, that can be used with electroencephalography EEG, electromyography EMG, or electronystagmography ENG sensors. The openings or panels 32, 34, 36, and 38 permit cables attached to the sensor to be passed through the support assembly 20 and connected to their consoles.

Infant/Juvenile Head Coil

Figure 10A:
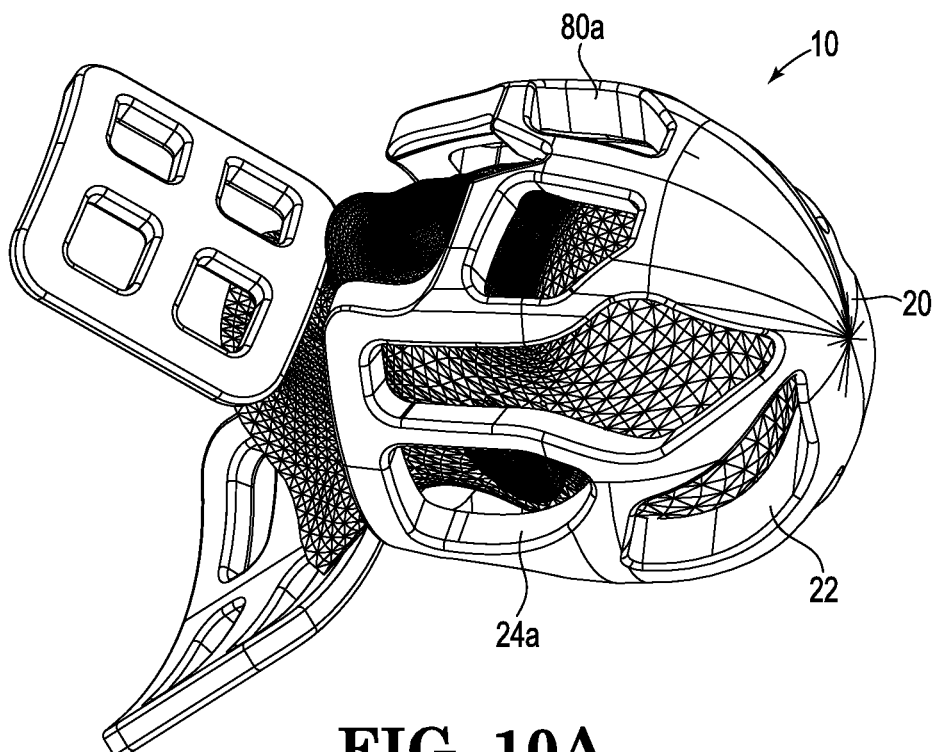
FIG. 10A is a perspective view of an infant or juvenile wearable open and adjustable head coil, according to an example embodiment of the present invention.
Figure 10B:
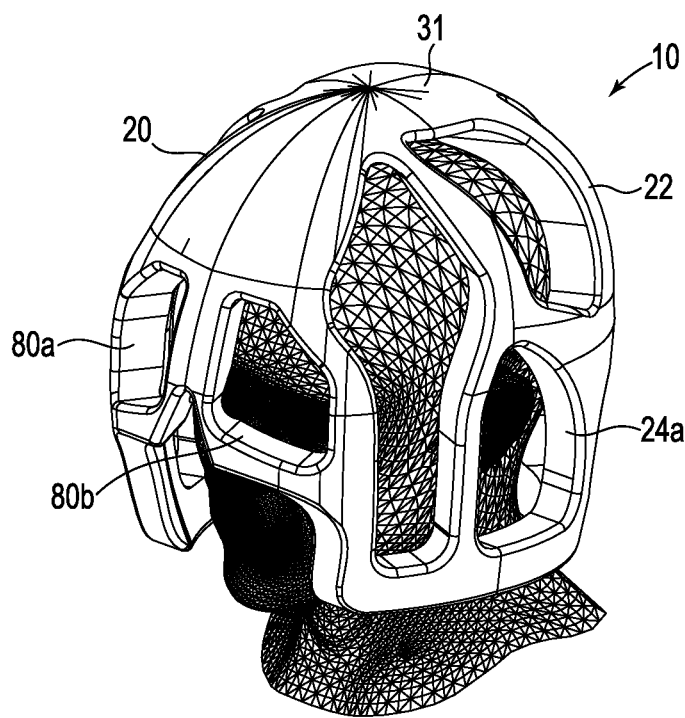
FIG. 10B is a perspective view of an infant or juvenile wearable open and adjustable head coil, according to an example embodiment of the present invention.
Figure 10C:
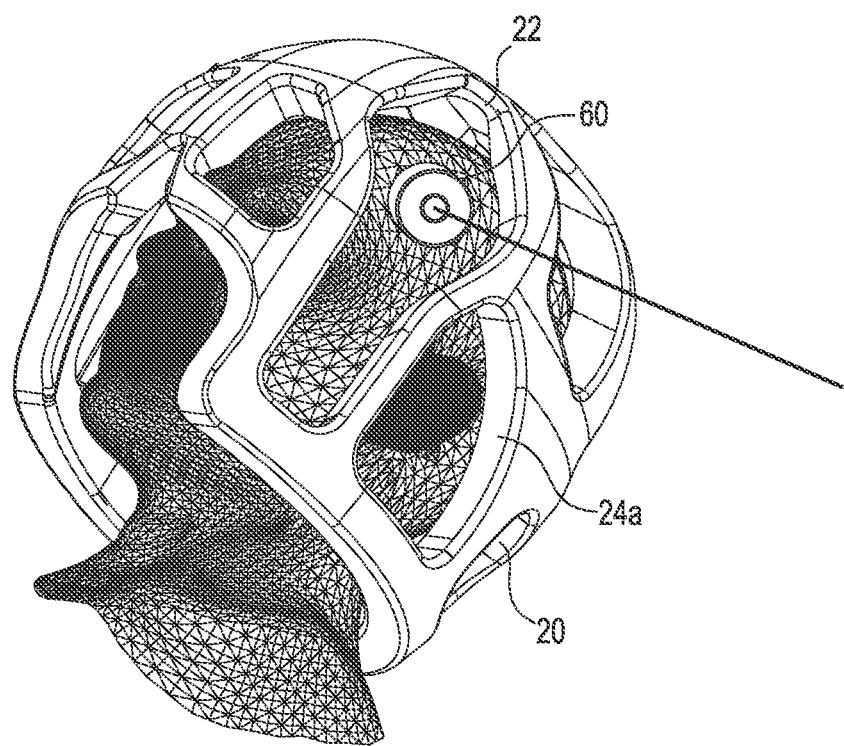
FIG. 10C is a perspective view of a wearable open and adjustable head coil with an ultrasound transducer, according to an example embodiment of the present invention.

In yet another example embodiment, as illustrated in FIGS. 10A-10B, the support assembly 20 is sized and shaped to fit an infant or juvenile. The support assembly 20 of the infant head coil 12 is capable of housing, encasing, or supporting radiofrequency receiver antennae or imaging coils 40 that receive MRI radiofrequency signals for imaging process. The support assembly may include openings 22, 24*a* and 24*b*, 26, and 28 and may comprise an elastic or compressible material that enables the openings 22, 24*a* and 24*b*, 26, and 28 to be moved, reshaped, or opened wider for increased access to various portions of the patient, including the patient's head. The adjustability of the size of the openings 22, 24*a* and 24*b*, 26, and 28 enables the support assembly 20 to accommodate different stabilizers, LIFUs, HIFUs, other sensors, and the like, used during therapy, surgery, or other interventional and therapeutic procedures.

The infant/juvenile head coil 12 also includes left and right eye openings 80*a* and 80*b*, respectively, that are positionable over the infant's or juvenile's eyes when worn. The eye openings 80*a* and 80*b* permit the patient to be able to see while providing added protection (e.g., for embodiments having a cushioning or compressible material). Similar to other embodiments, the head coil 12 does not cover a mouth of a patient, which permits medical staff to quickly place and remove medical devices and life supportive devices, such as ventilators, respirators, oxygen masks, tubes, catheters, electrodes, cervical collars, halos, probes, and other devices. The ability to quickly and easily place or remove medical equipment while a patient, especially an infant, undergoes diagnostic, therapeutic, and surgical procedures is a significant advantage over conventional birdcage head coils.

Continuing with FIGS. 10A-10B, the present invention also includes pre-formed or flexibly positionable surface coils 82 and 84. The pre-formed or flexibly positionable surface coils 82 and 84 may be manufactured from the materials described herein. They may also include a semi-rigid or flexible member that can be flexed or bent into a desired position or configuration, such as around a patient's neck, back, chest, or any other anatomy. The pre-formed or flexibly positionable surface coils 82 and 84 also include radiofrequency receiver antennae or imaging coils 40 on their surface, or housed therein, that are removably connectable to a preamp 50. The pre-formed or flexibly positionable surface coils 82 and 84 may also include one or more openings 86 that provide access to placement of diagnostic, therapeutic, and/or surgical devices. Similar to the head coils described herein, the diagnostic, therapeutic, and surgical devices can be placed flush on the surface of the patient simultaneously with the radiofrequency receiver antennae or imaging coils 40.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An MRI imaging assembly that is wearable about a head of a patient for use during medical procedures, the MRI imaging assembly comprising:
   an adjustable wearable open-framework MRI coil support adapted to form about the head of the patient, the adjustable MRI coil support having a plurality of pliable support members defining one or more access openings;
   one or more pliable MRI imaging coils housed within one or more pliable support members amongst the plurality of pliable support members, the one or more pliable MRI imaging coils adjustably positionable proximate to a surface of the head of the patient by adjustment of the one or more pliable support members, the adjustment of the one or more pliable support members defining a size or a shape of an access opening amongst the one or more access openings; and
   one or more ultrasound transducers mechanically integrated with a corresponding support member amongst the plurality of pliable support members, the one or more ultrasound transducers positionable to establish an ultrasound transducer in a location to provide a surface of the ultrasound transducer that is flush against a surface of the head of the patient.

2. The MRI imaging assembly of claim 1, wherein the plurality of pliable support members comprise a pliable material to conform about the head of the patient, the one or more pliable MRI imaging coils pliable within the pliable material.

3. The MRI imaging assembly of claim 1, further comprising one or more sensors located on or within the adjustable wearable open-framework MRI coil support, the one or more sensors configured to monitor a physiologic signal.

4. The MRI imaging assembly of claim 3, further comprising a respective fastener disposed on an inner surface of the adjustable wearable open-framework MRI coil support, wherein a respective sensor amongst the one or more sensors is removably connectable to the respective fastener.

5. The MRI imaging assembly of claim 1, wherein the one or more ultrasound transducers and the one or more pliable MRI imaging coils are sized and shaped for positioning proximate to a surface of the head of the patient to provide delivery of ultrasonic energy and MRI imaging.

6. The MRI imaging assembly of claim 1, wherein the one or more ultrasound transducers and the one or more pliable MRI imaging coils are sized and shaped for positioning substantially against a surface of the head of the patient to provide delivery of ultrasonic energy and MRI imaging.

7. The MRI imaging assembly of claim 1, further comprising one or more interventional or fixation devices, other than the one or more ultrasound transducers mechanically integrated with corresponding support members.

8. The MRI imaging assembly of claim 7, wherein the one or more interventional or fixation devices are adjustable for contact with a surface of the head of the patient contemporaneously with the adjustable wearable open-framework MRI coil support.

9. The MRI imaging assembly of claim 1, wherein the one or more pliable support members housing the one or more pliable imaging coils comprise a semi-rigid foam material.

10. The MRI imaging assembly of claim 1, wherein the access opening is defined by a closed loop formed by the one or more pliable support members.

11. A wearable MRI imaging system that is wearable about a head of a patient for use during therapeutic procedures, the wearable MRI imaging system comprising:
   an adjustable wearable open-framework MRI coil support adapted to be worn on a head of a patient, the adjustable wearable open-framework MRI coil support having a plurality of pliable support members, the plurality of pliable support members defining one or more access openings;
   one or more pliable NMI imaging coils enshrouded within one or more pliable support members amongst the plurality of pliable support members such that the one or more pliable MRI imaging coils are adjustably positionabie flush with a surface of the head of the patient when worn, by adjustment of the one or more of the plurality of pliable support members, the adjustment of the one or more of the plurality of pliable support members defining a size or a shape of an access opening amongst the one or more access openings; and
   one or more ultrasound transducers mechanically integrated with a corresponding support member amongst the plurality of pliable support members to establish an ultrasound transducer in a location to provide a surface of the ultrasound transducer that is flush with a surface of the head of the patient;
   wherein the one or more pliable MRI imaging coils and one or more ultrasound transducers are sized and shaped for positioning flush with the surface of the head of the patient when worn to facilitate MRI imaging contemporaneously with delivery of ultrasonic energy.

12. The wearable MRI imaging system of claim 11, further comprising one or more sensors attachable to the adjustable wearable open-framework MRI coil support, the one or more sensors configured to monitor a physiologic signal.

13. The wearable MRI imaging system of claim 11, further comprising one or more interventional or fixation devices, other than the one or more ultrasound transducers mechanically integrated with corresponding support members.

14. The wearable MRI imaging system of claim 13, wherein the one or more interventional or fixation devices are adjustable for contact with a surface of the head of the patient contemporaneously with the adjustable wearable open-framwork MRI coil support and the one or more ultrasound transducers.

15. The wearable MRI imaging system of claim 11, wherein the one or more pliable support members housing the one or more pliable imaging coils comprise a semi-rigid foam material.

16. A wearable MRI imaging system for use during therapeutic procedures, the wearable MRI imaging system comprising:
   an adjustable wearable open-framework MRI coil support adapted to worn on a head of a patient, the adjustable wearable open-framework MRI coil support having a plurality of pliable support members, the plurality of pliable support members defining one or more access openings;

one or more pliable MRI imaging coils supported by one or more pliable support members amongst the plurality of pliable support members such that the one or more pliable MRI imaging coils are adjustably positionable substantially proximate to a surface of the head of the patient when worn, by adjustment of the one or more of the plurality of pliable support members, the adjustment of the one or more pliable support members defining a size or a shape of an access opening amongst the one or more access openings;

one or more ultrasound transducers mechanically integrated with a corresponding support member amongst the plurality of pliable support members to establish an ultrasound transducer in a location to provide a surface of the ultrasound transducer that is proximate to a surface of the head of the patient; and a preamp adapted to receive and amplify a signal from at least one MRI imaging coil amongst the one or more pliable MRI imaging coils;

wherein the one or more pliable MRI imaging coils and one or more ultrasound transducers are sized and shaped for positioning proximate to the surface of the head of the patient when worn.

17. The wearable MRI imaging system of claim 16, further comprising one or more sensors attachable to the adjustable wearable open-framework MRI coil support, the one or more sensors configured to monitor a physiologic signal.

18. The wearable MRI imaging system of claim 17, further comprising a respective fastener disposed on an inner surface of the adjustable wearable open-framework MRI coil support, wherein a respective sensor amongst the one or more sensors is removably connectable to the respective fastener.

19. The wearable MRI imaging system of claim 16, further comprising one or more interventional or fixation devices, other than the one or more ultrasound transducers mechanically integrated with corresponding support members.

20. The wearable MRI imaging system of claim 19, wherein the one or more interventional or fixation devices are adjustable for contact with a surface of the head of the patient contemporaneously with the adjustable wearable open-framework MRI coil support and the one or more ultrasound transducers.

21. The wearable MRI imaging system of claim 16, further comprising one or more surface coils positionable against a portion of the patient, the one or more surface coils being connectable to the preamp and in communication with the preamp.

22. The wearable MRI imaging system of claim 16, wherein the one or more pliable support members housing the one or more pliable imaging coils comprise a semi-rigid foam material.

\* \* \* \* \*

UNITED STATES PATENT AND TRADEMARK OFFICE
CERTIFICATE OF CORRECTION

| | | |
|---|---|---|
| PATENT NO. | : 11,839,447 B2 | Page 1 of 1 |
| APPLICATION NO. | : 16/617350 | |
| DATED | : December 12, 2023 | |
| INVENTOR(S) | : Rheineck et al. | |

It is certified that error appears in the above-identified patent and that said Letters Patent is hereby corrected as shown below:

On the Title Page

In item (72), in "Inventors", in Column 1, Line 4, delete "(MN);" and insert --MN (US);-- therefor In item (72), in "Inventors", in Column 1, Line 7, delete "MN" and insert --WI-- therefor In the Claims In Column 16, Line 21, in Claim 11, delete "NMI" and insert --MRI-- therefor In Column 16, Line 25, in Claim 11, delete "positionabie" and insert --positionable-- therefor Signed and Sealed this
Thirtieth Day of January, 2024

*Katherine Kelly Vidal*

Katherine Kelly Vidal
*Director of the United States Patent and Trademark Office*